(12) United States Patent
Charous

(10) Patent No.: US 6,572,858 B1
(45) Date of Patent: Jun. 3, 2003

(54) USES FOR ANTI-MALARIAL THERAPEUTIC AGENTS

(75) Inventor: B. Lauren Charous, Fox Point, WI (US)

(73) Assignee: APT Pharmaceuticals, LLC, Tucson, AZ (US)

( * ) Notice: Subject to any disclaimer, the term of this patent is extended or adjusted under 35 U.S.C. 154(b) by 0 days.

(21) Appl. No.: 09/563,267

(22) Filed: May 1, 2000

Related U.S. Application Data
(60) Provisional application No. 60/132,008, filed on Apr. 30, 1999.

(51) Int. Cl.[7] ......................... A61K 39/00; A61K 39/38; A61K 45/00; A01N 61/00
(52) U.S. Cl. .............................. 424/184.1; 424/278.1; 424/279.1; 514/1
(58) Field of Search ........................... 424/1.13, 174.1, 424/184.1, 278.1, 279.1; 514/1

(56) References Cited

U.S. PATENT DOCUMENTS
4,181,725 A    1/1980    Voorhees et al.

OTHER PUBLICATIONS

Barnes, Peter J., "Asthma Therapy with Aerosols: Clinical Relevance for the Next Decade", *Journal of Aerosol Medicine*, vol. 9, No. 1, 1996, pp. 131–141.
Busse, William W., et al., "Treatment Regimen and Side Effects of Treatment Measures", *Am. J. Respir. Crit. Care Med.*, vol. 149, pp. S44–S50, 1994.
Charous, Lauren B., "Open study of hydroxychloroquine in the treatment of severe symptomatic or corticosteroid–dependent asthma", *Annals. of Allergy*, vol. 65, Jul., 1990, pp. 53–58.
Charous, Lauren B., et al., "Hydroxychloroquine improves airflow and lowers circulating IgE levels in subjects with moderate symptomatic asthma", *J. Allergy Clin. Immunol.*, vol. 102, No. 2, 1998, pp. 198–203.
Charous, Lauren B., "Effectiveness of Long–Term Treatment of Severe Asthma with Hydroxychloroquine (HCQ)", *Annals. of the New York Academy of Sciences*, vol. 629, pp. 432–433. 1991.
Charous, Lauren B., et al., "Double–blind Trial of Hydroxychloroquine (HCQ) as Anti Allergic Anti–Asthmatic Therapy", *J. Allergy Clin. Immunol.*, Jan. 1997.
Charous, Lauren B., "Long–Term Treatment of Severe Asthma with Hydroxychloroquine", *Annals of Allergy*, vol. 68, No. 1, p. 80, 1992.
Charous, Lauren B., "Double–blind Trial of Hydroxychloroquine (HCQ) As Anti–Allergic Anti–Asthmatic Therapy", *J. Allergy Clin. Immunol.*, Jan. 1997, p. S268.
Cockcroft, D.W., "Therapy for airway inflammation in asthma", *J. Allergy Clin. Immunol.*, May 1991, vol. 87, No. 5. pp. 914–919.
Fox, Robert I., et al., "Treatment of Primary Sjogen's Syndrome with Hydroxychloroquine", *The American Journal of Medicine*, vol. 85, 1998, p. 62–67.
Goldstein, Jay A., "Hydroxychloroquine for Asthma", *Am. Rev. Res. Diseases*, 128(6):1100–1101. 1983.
Landwehr, Lawrence P., et al., "Management of Steroid–Resistant Asthma", *Clin. Immunother.*, 4(2) 1995, pp. 124–137.
Ledford, Dennis K., "Alternative Treatments for Severe, Chronic Asthma", *Allergy Proc.*, Jan.–Feb. 1993, vol. 14, No. 1, pp. 23–30.
Ledford, Dennis K., "Treatment of Steroid–Resistant Asthma", *Immunology and Allergy Clinics of North America*, vol. 16, No. 4, Nov. 1996, pp. 777–796.
Moss, Richard B., "Alternative Pharmacotherapies for Steroid–Dependent Asthma", *Chest*, vol. 107, No. 3, Mar. 1995, pp. 817–825.
Ornstein, Matthew H., et al., "The Anti–Inflammatory and Antiviral Effects of Hydroxy–Chloroquine (HCQ) in 2 Patients with Aids and Active Inflammatory Arthritis", *Arthritis & Rheumatism*, vol. 38, No. 9, p. S198.
Roberts, J.A., et al., "Effect of Hydroxychloroquine in Chronic Steroid Dependent Asthma", *J. Allergy Clin. Immune*, 1986, vol. 77, No. 1, Part 2, p. 151.
Roberts, J.A., et al., "Hydroxychloroquine in Steroid Dependent Asthma", *Pulmonary Pharmacology*, 1998, p. 59–61.
Seggey, J.S., et al., "Inhibition of IL–4–Driven IgE Synthesis by Peripheral Blood Lymphocytes (PBL) in vitro with Hydroxychloroquine (HCQ)", *Allergic Disease IgE*, No. 343, p. 62A. 1993.
Sherman, et al., "Short–Term Effects of Hydroxychloroquine (HCQ) on IgE Levels and Obstructive Airways Disease", *J. Allergy Clin. Immunol.*, Jan. 1992, No. 567, p. 286.
Sorkness, Christine, et al., "Alternatives to Corticosteroids in the Treatment of Asthma", *Immunology and Allergy Clinics of North America*, vol. 13, No. 4, Nov. 1993, p. 917–938.

*Primary Examiner*—Mark Navarro
(74) *Attorney, Agent, or Firm*—Scully, Scott, Murphy & Presser

(57) ABSTRACT

A diversity of inflammatory diseases can be treated via local delivery to the patient of a composition containing a therapeutically effective amount of an anti-malarial agent. In a preferred embodiment of the method of the invention, a pulmonary inflammatory condition, such as asthma, is treated by inhalation of an aerosolized anti-malarial agent, such as hydroxychloroquine.

9 Claims, 10 Drawing Sheets

USES FOR ANTI-MALARIAL THERAPEUTIC AGENTS

RELATED APPLICATION

Figure 1:
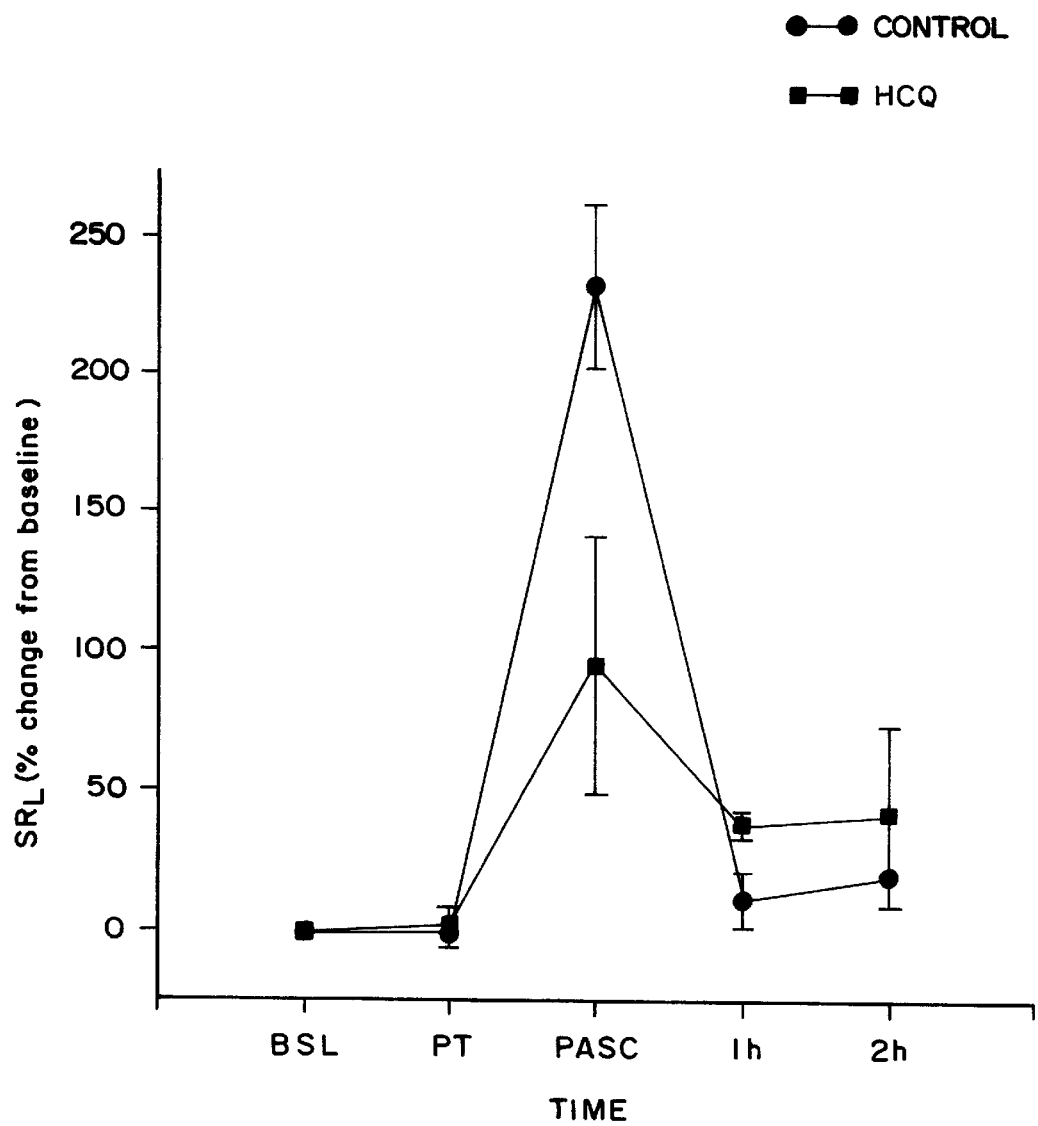

The present application claims benefit of U.S. patent application Ser. No. 60/132,008 filed on Apr. 30, 1999.

FIELD OF THE INVENTION

The present invention relates to a method for treating inflammatory conditions including pulmonary diseases states, such as asthma using anti-malarial agents via non-systemic administration.

BACKGROUND OF THE INVENTION

Inflammation is a phenomenon encountered in a variety of situations, including infections, transplantations, auto-immune disorders and following injury. There exists an immense range of distinct inflammatory reactions, each of which utilizes various immune mechanisms, such as memory T-cell and B-cells; cytokines and interleukins; preformed and synthesized chemical mediators, such as histamine, prostaglandins and leukotrienes; antibodies of different classes, as well as a whole host of disparate effector cells (e.g., killer cells, macrophages, neutrophils, basophils, eosinophils and the like).

Inflammatory diseases are among the most common maladies today. For example, asthma, a chronic inflammatory disorder of the airways, affects approximately 6–7% of the population of the U.S. (an estimated 17 million, according to a 1998 CDC forecast) and similar figures have been reported in other countries.

Asthma is a lung disease with the following characteristics: (1) airway obstruction that is reversible (but not completely so in some patients) either spontaneously or with treatment; (2) airway inflammation and (3) increased responsiveness to a variety of stimuli.

Airway inflammation contributes to the airway hyperresponsiveness, airflow limitation, respiratory symptoms and disease chronicity, which are characteristic of asthma (see Guidelines For The Diagnosis And Management of Asthma, Expert Panel Report 2, April 1997, NHLBI, NIH, Publication No. 97-4051, p.1). Asthma results from complex multi-cellular interactions among inflammatory cells, mediators, and other cells and tissues resident in the airway. Chronic inflammation of the airways is also a major cause of bronchial constriction, bronchial epithelial edema and mucus secretory abnormalities. Persistent airway inflammation is thought to lead to sub-basement membrane fibrosis which may cause permanent airway remodeling and chronic irreversible airway obstruction.

For these reasons, recent recommendations for asthma therapy have centered on the use of anti-inflammatory therapy. Anti-inflammatory therapy is designed to reduce the number of activated inflammatory cells, such as neutrophils, eosinophils, mast cells and lymphocytes and mediators such as cytokines and chemokines in airway tissues or secretions. Therapeutics that have been used in the treatment of airway inflammation include: glucocorticosteroids, cromones, theophylline and leukotriene modifiers (Inflammation in asthma: the cornerstone of the disease and target of therapy, W W. Busse, 1998, *J. Allergy Clin. Immunol.* 102, S17–S22.).

Human glucocorticoid hormones of the adrenal cortex and their synthetic analogues have been the most widely adopted class of therapeutic agents used to treat a wide range of inflammatory conditions such as rheumatoid arthritis, lupus, inflammatory bowel disease, and asthma. These agents act via specific glucocorticoid membrane receptors found on a wide variety of cells, including those mediating inflammation. Once bound to the cell, their effects are mediated by a well-defined sequences of steps (see Glucocorticosteroids, R P Schleimer, p. 638–660 in Allergy, Principles and Practice ed. E. Middleton, Mosby, St. Louis, 1998) which culminates in the association of the glucocorticoid-receptor complex with cellular nuclear chromatin with the subsequent suppression of inflammatory genes as well as other effects. These actions are manifest on both developing and mature cells. This allows the use of glucocorticoid agents in both systemic and topical forms, including oral, intravenous, depot intramuscular, ophthalmic drops, cutaneous ointment and cream, suppository, retention enema, nasal spray, and by inhalation.

Despite their short-term effectiveness, however, glucocorticoids have significant long-term shortcomings. Glucocorticoids do not appear to alter the underlying pathologic processes, and discontinuance is generally followed by increasing symptoms and evidence for renewed airway inflammation (Juniper 1991, *J. Allerg. Clin. Immunol.*, 87:483; Waalkens *Am. Rev. Resp. Dis.* 1993, 148:1252–57). Moreover, oral systemic corticosteroid treatment is complicated by multiple severe toxicities, including adrenal suppression, osteoporosis, cataract formation, glucose intolerance, obesity and hypertension.

Use of topical or organ-system directed delivery glucocorticosteroid hormones reduces but does not completely avoid all toxicity. For instance, even with inhaled glucocorticosteroids, there is a documented increased rate of cataract formation and growth retardation in children which is dose dependent. Furthermore, in many patients with more severe asthma, inhaled glucocorticosteroids appear to have efficacy only at elevated doses where significant systemic levels may appear via pulmonary absorption.

As a consequence of these shortcomings of glucocorticosteroids, a wide range of anti-inflammatory pharmaceuticals agents has been developed and proven effective for the treatment of a wide range of inflammatory diseases. These include anti-proliferative agents such as methotrexate which is used for treating rheumatoid arthritis and systemic lupus erythematosus and 6-mercapto purine analogues used for treating inflammatory bowel disease; alkylating agents such as cyclophosphamide used for treating systemic vasculitis; long-acting immunosuppressive or immunomodulating agents such as cyclosporine which is used for treating transplant rejection and sarcoidosis; gold salts used for treating rheumatoid arthritis, dapsone used for treating urticaria and cutaneous vasculitis; colchicine used for treating vasculitis and gout; and hydroxychloroquine (HCQ) used as a systemic anti-malarial agent for treating rheumatoid arthritis, systemic lupus erythematosus, and primary Sjögren's syndrome. (Bell 1983, *Am. J. Medicine*, 75:46–51; Rothfield 1984, *Am. J. Med.*, 85:53–56; Fox 1984, *Am. J. Med.*, 85:62–67).

According to conventional usage, each and every one of these agents except HCQ has been administered systemically via oral or parenteral dosing only. HCQ has only been administered heretofore by oral dosing. Conversely, none has been dosed via a local, targeted administration, such as inhalational delivery, for several reasons. First, a large majority of these agents exert their effects on developing cells found in the marrow and spleen. Local, targeted administration cannot reach nor affect such cells; only with systemic administration can tissue levels sufficient to affect these cellular reservoirs be achieved. Second, unlike glucocorticosteroid hormones, a majority of these agents have little effect on mature inflammatory cells. Thus, local, targeted administration is not viewed as conveying any significant advantage in terms of therapeutic effect. Lastly, end organ toxicity resulting from exposure to these agents may be appreciable and even life-threatening. Inasmuch as some of this toxicity is expressed by mucosal or serosal epithelial surfaces (e.g., stomatitis due to methotrexate and gold salts; gastrointestinal toxicity due to colchicine; bladder carcinoma due to cyclophosphamide), local, targeted administration of such agents has been viewed as unjustified in terms of presumed increased risk and the lack of a known advantage associated with direct application.

As a consequence, trials using gold salts, dapsone, methotrexate, cyclosporine and hydroxychloroquine (HCQ) as well as other anti-inflammatory treatments of asthma have uniformly relied on oral dosing (see Bernstein, *J. Allerg. Clin.*, 1996, 98:317–24; Berlow, *J. Allerg. Clin. Immunol.*, 1991, 87:710–15; Mullarkey NEJM 988, 38 (10):603–607; Alexander, *Lancet*, 1992, 339:324–328; Charous, 1990, *Ann. Allergy*, 68:80). Even newer pharmaceutical agents such as leukotriene receptor antagonists (zafirlukast and montelukast) and monoclonal anti-IgE antibodies are systemically administered due to lack of efficacy of local, targeted administration.

Only the anti-inflammatory pharmaceuticals nedocromil and cromolyn sodium are administered as local, targeted agents (via inhalation) due to the fact that these agents are only poorly absorbed by the gastrointestinal tract after oral dosing. These agents are seen as having only "mild to moderate" activity as asthma therapeutics (see Guidelines for the Diagnosis and Management of Asthma, Expert Panel Report 2, April 1997, NHLBI, NIH, Publication No. 97-4051, p. 32).

Among the quinoline antimalarials (e.g., quinine, chloroquine, amodiaquine, primaquine and mefloquine) there are certain compounds which are used as anti-inflammatory therapeutics (Antimalarial pharmacokinetics and treatment regimens, N J White (1992) *Br. J. Clin. Pharmac.*, 34, 1–10). The 4-aminoquinoline class of antimalarial compounds, in particular chloroquine and hydroxychloroquine have been used as anti-inflammatory and immunomodulatory agents in the treatment of rheumatoid arthritis and systemic lupus erthematosus for the past 20 years. These compounds increase pH within intracellular vacuoles and alter processes such as protein degradation by acidic hydrolases, lipid mobilization and antigenic processing (Mechanism of Action of Hydroxychloroquine as an Antirheumatic Drug, R I Fox (1993) Seminars in Arthritis and Rheumatism, 23, Suppl. 1, 82–91). Although these drugs have been known for several years, they have been administered heretofore orally for specifically treating anti-inflammatory conditions.

Recently, U.S. Pat. No. 4,181,725 to Voorhees, et al. discloses the use of various drugs, such as chloroquine and hydroxychloroquine, for the treatment of skin proliferative diseases, such as psoriasis.

However, until now, no one has suggested administering these drugs locally for treating anti-inflammatory conditions which are not on the surface of the skin.

For example, as a systemically delivered immunomodulatory agent, hydroxychloroquine (HCQ) in particular has been demonstrated to have multiple anti-inflammatory effects and has been shown to have significant advantages in safety over the other available systemic anti-inflammatory agents mentioned above. For this reason, HCQ is the only systemic anti-inflammatory that has been approved, by both the FDA's Pulmonary Branch and an independent Investigational Review Board, for use in a double-blind trial in non-oral glucocorticosteroid-dependent asthmatic subjects (Hydroxychloroquine improves airflow and lowers circulating IgE levels in subjects with moderate symptomatic asthma, B. L. Charous, E. F. Halpern, G. C. Steven (1998), *J. Allergy Clin. Immunol.*, 102, 198–203).

The current delivery methods for HCQ, such as oral administration, have several drawbacks, however. When delivered orally, the rate of onset is slow, and the agent actively concentrates in organs other than the target organ. As a consequence, a relatively high dosage and long term treatment required. In addition to added cost and low efficiency such a high-dosage, long-term treatment carries a risk, however slight, of ocular toxicity. (Antimalarial ocular toxicity, a critical appraisal, D. A. Albert, L. K. L. Debois, K. F. Lu (1998) J. of Clin. Rheumatol. (US) 4, 57–62.)

Despite the drawbacks, the anti-malarials, such as HCQ, have only been administered systemically, e.g., orally for treating anti-inflammatory conditions, such as asthma, and topically on the surface of the skin for treating dermatological diseases, such as proliferative skin diseases. No one heretofore even suggested that they be administered by other means for treating anti-inflammatory conditions, especially since a change in the mode of administration may substantially alter drug action.

The choice of drug delivery methods requires full appreciation of the pharmacologic activities of the agent including tissue distribution, metabolism and cellular effects as well as an understanding of the interaction of the drug with the specific underlying pathological processes of the disease under treatment. Proof of efficacy by one route of administration does not imply the presence of a desired drug effect when administered via an alternate route of administration. For example, see, Fahy, et al. in *Am. J. Respir. Crit. Care Med.*, 1999, 160:1023–1027 which showed that intravenous administration of Anti IgE(E25) was effective for treating allergic asthma, but that a different route of administration, viz., inhalation, was virtually ineffective in treating allergic asthma. Moreover, a change in drug administration from systemic to methods designed to target drug delivery to affected tissues may substantially increase drug effects in selective tissue, but carries the risk of increased local toxicity. It may promote salutary effects such as decreasing the time to onset of action, but may result in loss of overall efficacy due to the restricted nature of tissue distribution.

Because the route of drug administration determines bioavailability and tissue levels and distribution, change in delivery may modify fundamentally the location, nature, extent and duration of anti-inflammatory actions, as well as alter dosing requirements and toxicities. As the skilled artisan is well aware, there can be no assumption that if a drug works when administered one way, it will work when administered another way, particularly when drugs are delivered to mucosal and serosal tissues. In effect, any change in administration method may cause undesired effects.

However, the present inventor has shown that when anti-malarials exhibiting anti-inflammatory activity are administered locally to a patient in need of treatment, the anti-malarials agents were unexpectedly more efficacious in treating inflammatory conditions than when administered systemically.

SUMMARY OF THE INVENTION

It is therefore an object of the present invention to provide a novel method for the administration of an anti-malarial agent that will reach the diseased area of the patient rapidly. Specifically, the present invention provides a method for treating an inflammatory condition, especially in the pulmonary system, comprising administering via localized delivery to an area of inflammation in a subject in need thereof, an anti-inflammatory effective amount of an anti-malarial compound thereto. An example of a particular application of the method of the invention is treatment of pulmonary inflammatory conditions, such as asthma, by inhalation of an aerosolized anti-malarial compound. The method of the invention unexpectedly shows a rapid, therapeutic effect compared to systemic administration.

It is another object of the present invention to provide for a kit comprising a pharmaceutical composition comprising an anti-malarial compound in effective amounts and a pharmaceutical carrier thereof, in combination with a inhaler or other device through which the preparation can be delivered in a targeted and localized manner, such as would occur by inhalation of an aerosolized preparation.

BRIEF DESCRIPTION OF THE DRAWINGS

FIG. 1 is an x-y plot of % change of $SR_L$ (specific lung resistance) from baseline over time. FIG. 1 shows the difference in $SR_L$ between HCQ treated sheep and historical controls immediately after antigen challenge.

FIG. 2 is an x-y plot of % change of $SR_L$ (specific lung resistance) from baseline over time. FIG. 2 shows the difference in late phase asthmatic reaction between HCQ treated sheep and historical controls.

FIG. 3 is a bar graph showing the baseline and post-antigen challenge differences in carbachol reactivity (PC 400 as measured in breath units) between HCQ treated sheep and historical controls.

FIG. 4A graphically represents a time course of antigen-induced changes in specific lung resistance ($SR_L$) in three sheep treated with aerosol HCQ, twice a day. Responses are compared to the animals' historical control (Control 1) and a two week follow-up control (Control 2).

FIG. 4B graphically show the effect of HCQ on airway responsiveness. BSL baseline PA is 24 h post antigen. A decrease in the $PC_{400}$ indicates the development of airway hyperresponsiveness. Values are mean±se for 3 sheep. Statistical analysis is found in Table 3.

FIG. 5A graphically shows a time course of antigen-induced changes in specific lung resistance ($SR_L$) in three sheep treated with oral HCQ, twice a day. Responses are compared to the animals' historical control (Control 1) and a two week follow-up control (Control 2).

FIG. 5B graphically shows the effect of HCQ on airway responsiveness. BSL=baseline, PA=24 h post antigen. A decrease in the $PC_{400}$ indicates the development of airway hyperresponsiveness. Values are mean±se for 3 sheep. Statistical analysis is found in Table 3.

FIG. 6A graphically shows the time course of antigen-induced changes in specific lung resistance ($SR_L$) in three sheep treated with aerosol HCQ, once a day. Responses are compared to the animals' historical control (Control 1) and a two week follow-up control (Control 2).

FIG. 6B graphically demonstrates the effect of HCQ on airway responsiveness. BSL baseline PA=24 h post antigen. A decrease in the $PC_{400}$ indicates the development of airway hyperresponsiveness. Values are mean±se for 3 sheep. Statistical analysis is found in Table 3.

FIG. 7A graphically shows the time course of antigen-induced changes in specific lung resistance ($SR_L$) in three sheep treated with differing doses of aerosol HCQ, once a day.

FIG. 7B demonstrates graphically the effect of HCQ on airway responsiveness. BSL baseline PA=24 h post antigen. A decrease in the $PC_{400}$ indicates the development of airway hyperresponsiveness. Values are mean±se for 3 sheep. Statistical analysis is found in Table 3.

FIG. 8 graphically shows the mean percent (%) protection of late airway response (LAR) and airway hyperresponsiveness (AHR) with differing doses of aerosol HCQ. Values are mean for 3 sheep.

FIG. 9A graphically shows the time course of antigen-induced changes in specific lung resistance ($SR_L$) in three sheep treated with aerosol HCQ, once daily for 4 weeks. Responses are compared to the animals' historical control (Control) and follow-ups 2 and 4 weeks after stopping drug treatment.

FIG. 9B shows graphically the effect of HCQ on airway responsiveness. BSL baseline PA=24 h post antigen. A decrease in the $PC_{400}$ indicates the development of airway hyperresponsiveness. Values are mean±se for 3 sheep. Statistical analysis is found in Table 3.

FIG. 10 graphically demonstrates the mean percent (%) protection of late airway response (LAR) and airway hyperresponsiveness (AHR) over time. Values are mean for 3 sheep.

DETAILED DESCRIPTION OF THE INVENTION

The present inventor has discovered that an anti-malarial agent administered in a local or targeted fashion, directly to the diseased organ or area of inflammation of a patient, is much more effective and efficacious than when administered orally with the result that the agent reaches a therapeutic level with surprising rapidity, in the targeted tissue or organ, while undesirable side effects are minimized. Accordingly, the present invention relates generally to the treatment of inflammatory conditions or disease states by local administration of an anti-inflammatory effective amount of an anti-malarial agent. By anti-malarial, as used herein, it is meant that the drug has been historically belonged to the class of drugs known as anti-malarials. Preferred antimalarials include aminoquinolines especially 8- and 4-aminoquinolines, acridines, e.g., 9-amino acridines and quinoline methanols, e.g., 4-quinolinemethanols.

Compounds used in the Invention

Compounds suitable for the present invention are anti-malarial agents that have immunomodulatory and anti-inflammatory effects. Anti-malarial agents are well known in the art. Examples of anti-malarial agents can be found, for example, in GOODMAN AND GILMAN'S: THE PHARMACOLOGICAL BASIS OF THERAPEUTICS, chapters 45–47, pages 1029–65 (MacMillan Publishing Co. 1985), hereby incorporated by reference.

The preferred anti-malarial compounds are quinine based or are aminoquinolines, especially 4- and 8-amino quinolines. An especially preferred class of antimalarials has a core quinoline structure (examples are mefloquine and quinine) which is usually substituted at one or more positions, typically at least at the 4- and/or 8-positions. One skilled in the art would understand that such agents could be administered in derivatized forms, such as pharmaceutically acceptable salts, or in a form that improves their pharmacodynamic profiles, such as esterification of acid or alcohol substituents with lower alkyls (e.g., $C_{1-6}$) or lower alkanoyloxy

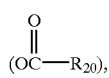

respectively, wherein $R_{20}$ is lower alkyl. Another class of antimalarials, exemplified by quinacrine, is based on an acridine ring structure, and may be substituted in the manner described above.

Especially preferred compounds for use in the present invention are aminoquinolines, including 4-amino and 8-aminoquinolines and their derivatives (collectively, "aminoquinoline derivatives") and aminoacridines, especially 9-amino acridines. The preferred 4- and 8 aminoquinolines and 9-amino acridines are described by the following formula:

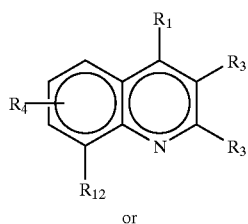

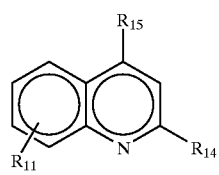

or pharmaceutically acceptable salts thereof, wherein $R_2$ and $R_3$ are independently hydrogen, or lower alkyl or $R_2$ and $R_3$ taken together with the carbon atoms to which they are attached form an aryl ring, which ring may be unsubstituted or substituted with an electron withdrawing group or an electron donating group, one of $R_1$ and $R_{12}$ is $NHR_{13}$ while the other is hydrogen;

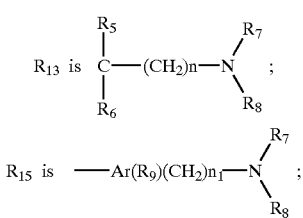

$R_4$, $R_{10}$, $R_{11}$ and $R_{14}$ are independently hydrogen or an electron donating group or electron withdrawing group;

$R_5$ and $R_6$, are independently hydrogen or lower alkyl which may be unsubstituted or substituted with an electron withdrawing or electron donating group;

$R_7$ and $R_8$ are independently hydrogen or lower alkyl, which may be unsubstituted or substituted with an electron withdrawing or electron donating group;

Ar is aryl having 6–18 ring carbon atoms;

$R_9$ is hydrogen or hydroxy or lower alkoxy or

$R_{25}$ is lower alkyl or hydrogen; and n and $n_1$ are independently 1–6.

As used herein, the terms "electron donating groups" and "electron withdrawing groups" refer to the ability of a substituent to donate or withdraw an electron relative to that of hydrogen if the hydrogen atom occupied the same position in the molecule. These terms are well understood by one skilled in the art and are discussed in Advanced Organic Chemistry, by J. March, John Wiley & Sons, New York, N.Y., pp. 16–18 (1985) and the discussion therein is incorporated herein by reference. Electron withdrawing groups include halo, including bromo, fluoro, chloro, iodo and the like; nitro; carboxy; carbalkoxy; lower alkenyl; lower alkynyl; formyl; carboamido; aryl; quaternary ammonium compounds, and the like. Electron donating groups include such groups as hydroxy; lower alkoxy; including methoxy; ethoxy and the like; lower alkyl, such as methyl; ethyl, and the like.; amino; lower alkylamino; diloweralkylamino; aryloxy, such as phenoxy and the like; arylalkoxy, such as benzyl and the like; mercapto, alkylthio, and the like. One skilled in the art will appreciate that the aforesaid substituent may have electron donating or electron withdrawing properties under different chemical conditions.

The term alkyl, when used alone or in conjunction with other groups, refers to an alkyl group containing one to six carbon atoms. It may be straight-chained or branched. Examples include methyl, ethyl, propyl, isopropyl, butyl, sec-butyl, isobutyl, tert-butyl, pentyl, neopentyl, hexyl and the like.

Lower alkoxy refers to an alkyl group which is attached to the main chain by an oxygen bridging atom. Examples include methoxy, ethoxy, and the like.

Lower alkenyl is an alkenyl group containing from 2 to 6 carbon atoms and at least one double bond. These groups may be straight chained or branched and may be in the Z or E form. Such groups include vinyl, propenyl, 1-butenyl, isobutenyl, 2-butenyl, 1-pentenyl, (Z)-2-pentenyl, (E)-2-pentyl, (Z)-4-methyl-2-pentenyl, (E)-4-methyl-2-pentenyl, allyl, pentadienyl, e.g., 1,3 or 2,4-pentadienyl, and the like. It is preferred that the alkenyl group contains at most two carbon-carbon double bonds; and most preferably one carbon-carbon double bond.

The term alkynyl include alkynyls containing 2 to 6 carbon atoms. They may be straight chain as well as branched. It includes such groups as ethynyl, propynyl, 1-butynyl, 2-butynyl, 1-pentynyl, 2-pentynyl, 3-methyl-1-pentynyl, 3-pentynyl, 1-hexynyl, 2-hexynyl, 3-hexynyl, and the like.

The term aryl refers to an aromatic group containing only carbon ring atoms which contains up to 18 ring carbon atoms and up to a total of 25 carbon atoms and includes the polynuclear aromatic rings. These aryl groups may be monocyclic, bicyclic, tricyclic, or polycyclic, and contain fused rings. The group includes phenyl, naphthyl, anthracenyl, phenanthranyl, xylyl, tolyl and the like.

The aryl lower alkyl groups include, for example, benzyl, phenethyl, phenpropyl, phenisopropyl, phenbutyl, diphenylmethyl, 1,1-diphenylethyl, 1,2-diphenylethyl and the like.

The term halo include fluoro, chloro, bromo, iodo and the like.

The preferred values of $R_2$ and $R_3$ are independently hydrogen or alkyl containing 1–3 carbon atoms. It is most preferred that $R_3$ is hydrogen. It is most preferred that $R_2$ is hydrogen or alkyl containing 1–3 carbon atoms, especially methyl or ethyl. It is most preferred that $R_2$ is hydrogen or alkyl containing 1–3 carbon atoms or hydrogen and $R_3$ is hydrogen.

Alternatively, if $R_2$ and $R_3$ are taken together with the carbon atoms to which they are attached, it is most preferred that they form a phenyl ring. The phenyl ring is preferably unsubstituted or substituted with lower alkoxy, hydroxy, lower alkyl or halo.

It is preferred that $R_4$ is an electron withdrawing group, more specifically, halo, especially chloro, or is hydroxy or lower alkoxy. It is even more preferred that when $R_1$ is $NHR_{13}$, $R_4$ is substituted on the 7-position of the quinoline ring. It is most preferred that when $R_1$ is $NHR_{13}$, $R_4$ is halo.

However, when $R_{12}$ is $NHR_{13}$, it is preferred that $R_4$ is an electron donating group, such as hydroxy or alkoxy. More specifically, it is preferred that $R_4$ is methoxy or ethoxy when $R_{12}$ is $NHR_{13}$. It is even more preferred that $R_4$ is on the 6-position of the quinoline ring when $R_{12}$ is $NHR_{13}$.

It is preferred that one of $R_5$ and $R_6$ is hydrogen and the other is lower alkyl. It is even more preferred that $R_5$ is hydrogen and $R_6$ is lower alkyl, especially alkyl containing 1–3 carbon atoms and most preferably methyl.

The preferred value of $R_7$ is lower alkyl, especially alkyl containing 1–3 carbon atoms and most preferably methyl and ethyl.

Preferred values of $R_8$ is lower alkyl containing 1–3 carbon atoms, and most preferably methyl and ethyl. However, it is preferred that the alkyl group is unsubstituted or if substituted, is substituted on the omega (last) carbon in the alkyl substituent. The preferred substituent is lower alkoxy and especially hydroxy.

The preferred $R_9$ is lower alkoxy and especially hydroxy.

$R_{11}$ is preferably an electron withdrawing group, especially trifluoromethyl. It is preferably located on the 8-position of the quinoline ring.

$R_{14}$ is preferably an electron withdrawing group, and more preferably trifluoromethyl. It is preferably present on the 2-position of the quinoline ring.

It is preferred that $R_{15}$ is

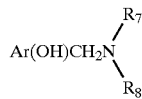

wherein $R_7$ and $R_8$ are independently alkyl containing 1–3 carbon atoms and Ar is phenyl.

In both $R_{13}$ and $R_{15}$, it is preferred that $R_7$ and $R_8$ contain the same number of carbon atoms, although one may be unsubstituted while the other is substituted. It is also preferred that $R_7$ and $R_8$ are the same.

The preferred value of n is 3 or 4 while the preferred value of $n_1$ is 1.

Preferred anti-malarials have the structure:

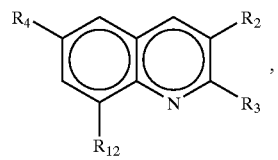

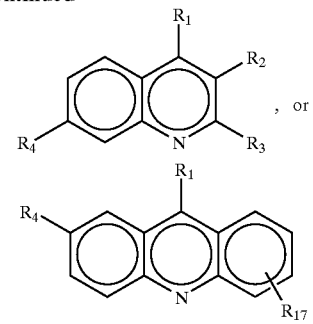

wherein $R_{12}$, $R_4$, $R_2$, $R_3$ and $R_1$ are as defined hereinabove and $R_{17}$ is hydrogen, halo, lower alkyl, lower alkoxy.

Preferred antimalarials include the 8-aminoquinolines, 9-aminocridines and the 7-chloro-4-aminoquinolines. Examples include pamaquine, primaquine, pentaquine, isopentaquine, quinacrine salts, 7-chloro-4-aminoquinolines, such as the chloroquines, hydroxychloroquines, sontoquine, amodiaquine and the like.

Another class of preferred antimalarial are cinchono alkaloids and 4-quinoline methanols, such as those having the formula:

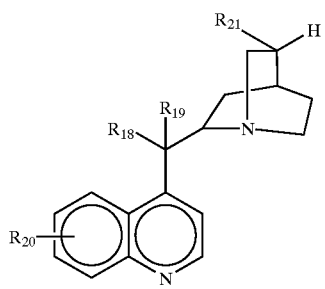

wherein one of $R_{18}$ and $R_{19}$ is hydroxy or loweralkylcarbonyloxy or hydrogen, and the other is H, and $R_{20}$ is hydrogen or loweralkoxy and $R_{21}$ is hydrogen or $CH=CH_2$.

Examples include rubane, quinine, quinidine, cinchoidine, epiquinine, epiquinidine, cinchonine, and the like.

Another preferred quinoline methanol is mefloquine or derivative thereof of the formula:

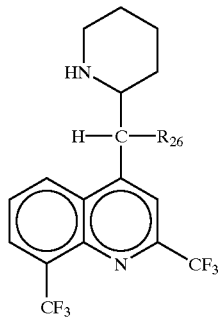

wherein $R_{26}$ is lower alkoxy,

and especially hydroxy and
$R_{27}$ is lower alkyl.

The most preferred anti-malarials include mefloquinine, and chloroquine and its congeners, such as hydroxychloroquine (HCQ), amodiaquine, pamaquine and pentaquine and pharmaceutically acceptable salts thereof.

The most preferred anti-malarial agent for the invention is hydroxychloroquine, shown below, or a pharmaceutically suitable salt thereof, such as hydroxychloroquine sulfate

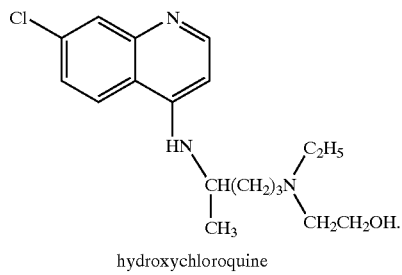

hydroxychloroquine

The antimalarials are commercially available or are prepared by art recognized techniques known in the art.

For example, the 4-aminoquinolines can be prepared as follows:

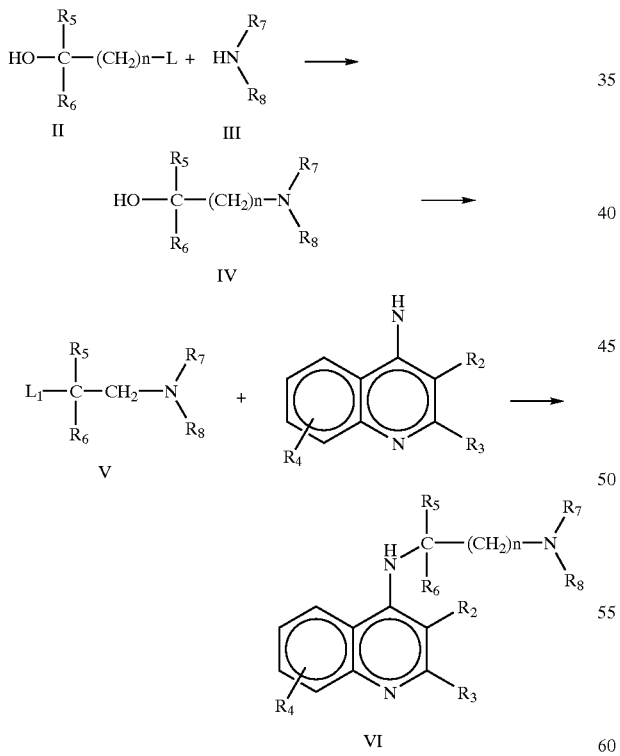

In the above scheme, $R_1$, $R_2$, $R_3$, $R_4$, $R_5$, $R_6$, $R_7$, $R_8$, and n are as defined hereinabove, and L and $L_1$ are good leaving groups, such as halides or sulfonates, e.g., mesylates or aryl sulfonates, e.g., tosylates, brosylates, and the like.

The compound of Formula II containing a leaving group, L, is reacted with the amine of Formula III under amine alkylation conditions. The alcohol group in the product of Formula IV (OH group) is converted to a leaving group by reactions known in the art. For example, sulfonic esters, such as tosylates, mesylates or brosylates are prepared by treatment of sulfonic halides of the formula $R_{23}SO_2X_1$ wherein $X_1$ is halide and $R_{23}$ is lower alkyl, such as methyl, aryl or substituted aryl, such as p-bromophenyl, p-tolyl with the alcohol of Compound IV. The reaction is usually effected in the presence of a weak base, such as pyridine. Alternatively, the alcohol can be converted to the corresponding halide by reaction of the alcohol of IV with HCl, HBr, thienyl chloride, $PCl_3$, $PCl_5$ or $POCl_3$. The product of V is then reacted under amine alkylation conditions with the quinoline amine to provide the 4-amino quinoline product.

The 9-aminoacridines and the 8-aminoquinoline are prepared similarly. More specifically, the product of V is reacted with

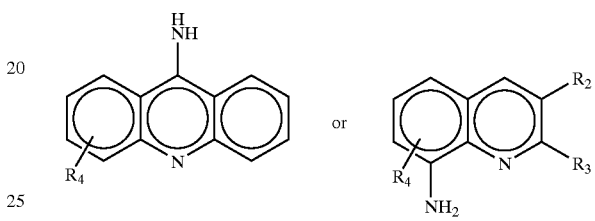

under amine alkylation reaction conditions.

The reactions described hereinabove are preferably conducted in solvents which are inert to the reactants and products and in which the reactants, are soluble, such as tetrahydrofuran, ethers, acetones, and the like. It is preferred that the solvents are volatile. The reactions are conducted at effective reaction conditions and are conducted at temperatures ranging from room temperature up to and including the reflux temperatures of the solvent.

An exemplary procedure for the preparation of compounds of Formula VII is as follows:

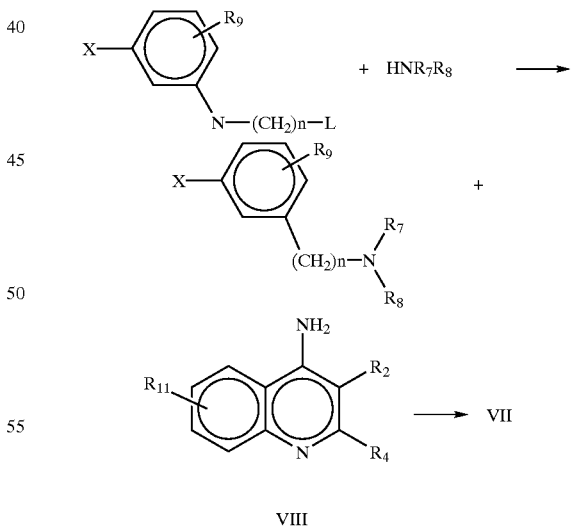

The first reaction is a simple amino alkylation reaction as described hereinabove. The product thereof is reacted with the amine of Formula III in the presence of a strong base such as amide to form the product of Formula VII.

Many of the compounds described hereinabove, especially the 4-quinoline methanols, can be converted to ethers by reacting the salt of the alcohols with an alkyl halide or arylalkyl halide or aryl halide to form the corresponding ether. Moreover, the esters can be formed from the hydroxy group by reacting the alcohol, such as the 4-quinoline methanol, with an alkanoic acid, arylalkonic acid or aryloic acid or acylating derivatives thereof in the presence of acid, for example, HCl, $H_2SO_4$ or p-toluene sulfonic acid under esterification conditions.

If any of the groups on $R_1$, $R_2$, $R_3$, $R_4$, $R_5$, $R_6$, $R_7$, $R_8$ are reactive with any of the reagents used or with any of the reactants or products, then they would be protected by protecting groups known in the art to avoid unwanted side reactions. This protecting groups normally used in synthetic organic chemistry are well known in the art. Examples are found in PROTECTIVE GROUPS IN ORGANIC SYNTHESIS, by T. W. Greene, John Wiley & Sons, Inc., NY 1981 ("Greene"), the contents of which are incorporated by reference.

Therapeutical Compositions of the Invention

A therapeutic composition within the present invention is formulated for localized (targeted) delivery and includes at least one anti-malarial agent, as described above. As previously emphasized, the present invention contemplates administration of the anti-malarial compounds to internal organs, such as the lungs, or the eye, or internal muscles or tissues, by local or targeted delivery. "Local or topical delivery" and "locally administering" are used in this description to denote direct delivery to the site, such that the therapeutic agent acts directly on affected tissue or the area of a diseased organ. Local delivery contrasts with methods by which a therapeutic agent is administered orally, or otherwise systemically, and is absorbed into the circulation for distribution throughout the patient's body. Examples of local delivery include inhalation, nasal spray, suppository, and eye drops and by injections directly to the organ, muscle or tissue. It is to be noted that the anti-malarial compound is not injected intravenously, that is, into the circulatory blood of the patient. Topical delivery to the skin, however, is not contemplated in the practice of "local or topical delivery" as defined above. These compositions may be solutions, suspensions and admixtures, for example. As one having ordinary skill in the art would understand, they may be prepared essentially as detailed in REMINGTON'S PHARMACEUTICAL SCIENCES, 18$^{th}$ ed., (Mack Publishing Co. 1990) ("Remingtons"), which is hereby incorporated by reference.

The compounds of the present invention are present in the pharmaceutical compositions in anti-inflammatory effective amounts. The anti-malarial compounds used in the present invention are administered in an amount which depends upon the condition of the subject, the type of inflammatory condition of which the subject suffers, the timing of the administration of the subject, the route of administration, the particular formulation and the like. However, unlike oral dosing which takes usually about a month before there is a noticeable or measurable onset of action, onset of action of the area of inflammation, from local administration of the anti-malarials is noticed or observed within 10 days after initial administration. Effective amounts of the anti-malarial compounds, hereinafter known as drug, is that amount which provides the observable onset of action within 10 days, and more preferably within 7 days after administration. Significantly less amount of drug is given locally than by systemic administration to achieve efficacious results, and the onset of action, as indicated hereinabove, is much faster by local administration. It is preferred that the drug is administered locally at a dosage of about 0.020 to about 2 mg/kg animal weight and more preferably from about 0.100 to about 1 mg/kg and most preferably from about 0.200 to about 0.650 mg/kg.

For pulmonary delivery, a therapeutic composition of the invention is formulated and administered to the patient in solid or liquid particulate form by direct administration e.g., inhalation into the respiratory system.

Solid or liquid particulate forms of the active compound prepared for practicing the present invention include particles of respirable size: that is, particles of a size sufficiently small to pass through the mouth and larynx upon inhalation and into the bronchi and alveoli of the lungs. In general, particles ranging from about 1 to 10 microns in size are within the respirable range. The therapeutic composition containing the anti-malarial compounds are preferably administered by direct inhalation into the respiratory system for delivery as a mist or other aerosol or dry powder. Particles of non-respirable size which are included in the aerosol tend to be deposited in the throat and swallowed; thus the quantity of non-respirable particles in the aerosol is preferably minimized.

The dosage of active compound via this route will vary depending on the condition being treated and the state of the subject, but generally may be an amount sufficient to achieve dissolved concentrations of anti-malarial compound on the airway surfaces of the subject. Depending upon the solubility of the particular formulation of active compound administered, the daily dose may be divided among one or several unit dose administrations. The daily dose by weight will depend upon the age and condition of the subject. Such a daily dose of the anti-malarial compound ranges from about 0.20 mg/kg per day to about as 2.0 mg per day, and more preferably from about 0.1 to about 1 mg/kg and most preferably from about 0.200 mg/kg to about 0.650 mg/kg. In the most preferred embodiments, only one dose is administered to the patient per day. The doses of the active compounds may be provided as one or several prepackaged units.

In the manufacture of a formulation according to the invention, the anti-malarial compounds or the pharmaceutically acceptable salts are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit dose formulation. One or more drugs may be incorporated in the formulations of the invention, which formulations may be prepared by any of the well-known techniques of pharmacy consisting essentially of admixing the drug with the other various components described hereinbelow present therein.

Aerosols of liquid particles comprising the anti-malarial compounds may be produced by any suitable means, such as inhalatory delivery systems. One is a traditional nebulizer which works in a mechanism similar to the familiar perfume atomizer. The airborne particles are generated by a jet of air from either a compressor or compressed gas cylinder passing through the device (pressure driven aerosol nebulizer). In addition, newer forms utilize an ultrasonic nebulizer by vibrating the liquid at speed of up to about 1 MHz. See, e.g., U.S. Pat. No. 4,501,729, the contents of which are incorporated by reference. Nebulizers are commercially available devices which transform solutions or suspensions of the active ingredient into a therapeutic aerosol mist either by means of acceleration of compressed gas, typically air or oxygen, through a narrow venturi orifice or by means of ultrasonic agitation. Suitable formulations for use in nebulizers consist of the active ingredient in a liquid carrier. The carrier is typically water (and most preferably sterile, pyrogen-free water) or a dilute aqueous alcoholic solution, preferably made isotonic but may be hypertonic with body fluids by the addition of, for example, sodium chloride. Optional additives include preservatives if the formulation is not made sterile, for example, methyl hydroxybenzoate, as well as antioxidants, flavoring agents, volatile oils, buffering agents and surfactants, which are normally used in the preparation of pharmaceutical compositions.

Aerosols of solid particles comprising the anti-malarial compound may likewise be produced with any solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the anti-malarial compound, a suitable powder diluent, such as lactose, and an optional surfactant. A second type of illustrative aerosol generator comprises a metered dose inhaler. Metered dose inhalers are pressurized aerosol dispensers, typically containing a suspension or solution formulation of the anti-malarial compound in a liquified propellant. During use these devices discharge the formulation through a valve, adapted to deliver a metered volume, from 10 to 22 microliters to produce a fine particle spray containing the antimalarial compound. Suitable propellants include certain chlorofluorocarbon (compounds, for example, dichlorodifluoromethane, trichlorofluoromethane, dichlorotetrafluoroethane and mixtures thereof. The formulation may additionally contain one or more co-solvents, for example, ethanol, surfactants, such as oleic acid or sorbitan trioleate, antioxidants and suitable flavoring agents.

Any propellant may be used in carrying out the present invention, including both chlorofluorocarbon-containing propellants and non-chlorofluorocarbon-containing propellants. Fluorocarbon aerosol propellants that may be employed in carrying out the present invention including fluorocarbon propellants in which all hydrogen are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Examples of such propellants include, but are not limited to: $CF_3CHFCF_2$, $CF_3CH_2CF_2H$, $CF_3CHFCF_3$, $CF_3CH_2CF_3$, $CF_3CHCl—CF_2Cl$, $CF_3CHCl—CF_3$, $CF_3CHCl—CH_2Cl$, $CF_3CHF—CF_2Cl$, and the like. A stabilizer such as a fluoropolymer may optionally be included in formulations of fluorocarbon propellants, such as described in U.S. Pat. No. 5,376,359 to Johnson.

Compositions containing respirable dry particles of micronized anti-malarial compounds may be prepared by grinding the dry active compound, with e.g., a mortar and pestle or other appropriate grinding device, and then passing the micronized composition through a 400 mesh screen to break up or separate out large agglomerates.

The aerosol, whether formed from solid or liquid particles, may be produced by the aerosol generator at a rate of from about 10 to 150 liters per minute. Aerosols containing greater amounts of medicament may be administered more rapidly. Typically, each aerosol may be delivered to the patient for a period from about 30 seconds to about 20 minutes, with a delivery period of about 1 to 5 minutes being preferred.

The particulate composition comprising the anti-malarial compound may optionally contain a carrier which serves to facilitate the formation of an aerosol. A suitable carrier is lactose, which may be blended with the active compound in any suitable ratio.

For example, hydroxychloroquine sulfate is a colorless crystalline solid which is readily soluble in water. Inhaled liquid forms may be formulated to contain such additives as are typically used in such pharmaceutical preparations, including, but not limited to an acceptable excipient and/or surfactant. A therapeutic composition of HCQ may be preformulated in liquid form, or prepared for the addition of a suitable carrier, like sterile water or physiological saline, immediately prior to use. The aerosol containing HCQ typically contain a propellant especially a fluorocarbon propellant. See Remington's, chapter 92. A particularly useful composition of HCQ is formulated in a nebulizer, for the treatment of a variety of pulmonary conditions. For the preparation of HCQ in inhaled powder form, the compound is finely divided, or micronized to enhance effectiveness, and admixed with a suitable filler. Inhaled powders may contain a bulking agent and/or stabilizer, as described hereinabove. Id., chapter 88. An insufflator (powder blower) may be employed to administer the fine powder.

The antimalarial compounds may be administered by other methods of local delivery, as defined herein. Compositions for these other mode of local delivery may include sterile aqueous solutions which may also contain buffers, diluents and other suitable additives and may be administered in other forms, such as oral pastes or ointment, retention enemas, suppositories, and injectable solutions, which injectable solutions are administered directly to internal organs or tissues and not intravenously.

The anti-malarial compounds may, where appropriate, be conveniently present in discrete unit dosage forms and may be prepared by any of the methods well known in the art of pharmacy. Such methods include the step of bringing into association the active compound, i.e., the anti-malarial compound with liquid carriers, solid matrices, semi-solid carriers, finely divided solid carriers or combinations thereof, and then, if necessary, shaping the product into the desired delivery system. Methods for admixing a pharmaceutical with a carrier are known in the art and are applicable to the present formulation.

The anti-malarial compounds may also be formulated as an ophthalmic product, like liquid eye drops or an ophthalmic ointment or nose drops or spray. See Remington's, Chapter 86. Drops, such as eye drops or nose drops, may be formulated with an aqueous or non-aqueous base also comprising one or more dispersing agents, solubilizing agents or suspending agents. Drops can be delivered via a simple eye dropper-capped bottle or eye-dropper, or via a plastic bottle adapted to deliver liquid contents dropwise, via a specially shaped closure. Ophthalmic preparations typically contain at least one compound in a sterile isotonic solution, for example, sodium chloride or boric acid. They may contain agents that increase viscosity, like methylcellulose, polyvinyl alcohol or hydroxymethyl cellulose.

The compounds also may be formulated advantageously as nasal sprays, oral pastes, ointments to be administered directly to the organ, such as the eye, and retention enemas, and other means known to one of ordinary skill in the art for local delivery.

Drugs can be administered by the lower enteral route, i.e., through the anal portal into the rectum or lower intestine. Rectal suppositories, retention enemas or rectal catheters can be used for this purpose. The drug may be administered in unit dose suppositories. Suitable carriers include cocoa butter and other materials commonly used in the art, and the suppositories may be conveniently formed by the admixture of the anti-malarial compounds with the softened or melted carriers followed by chilling and shaping into molds.

The pharmaceutical forms suitable for injectable use directly into muscle or tissue include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents, delaying absorption, for example, aluminum monostearate and gelatin.

Sterile injectable solutions are prepared by incorporating the anti-malarial compound in the required amount in the appropriate solvent with various of the other ingredients enumerated above, as required followed by filtered sterilization. Generally, dispersions are prepared by incorporating the sterilized anti-malarial compound into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the anti-malarial compound plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well-known in the art. Except insofar as any conventional media or agent is incompatible with the active ingredient, its use in the therapeutic compositions is contemplated. More than one anti-malarial compound can also be incorporated into the pharmaceutical compositions.

It is especially advantageous to formulate local compositions in dosage unit form for ease of administration and uniformity of dosage. Dosage unit form as used herein refers to physically discrete units suited as unitary dosages for the mammalian subjects to be treated; each unit containing a predetermined quantity of anti-malarial compound calculated to produce the desired therapeutic effect in association with the required pharmaceutical carrier. The specification for the novel dosage unit forms of the invention are dictated by and directly dependent on (a) the unique characteristics of the anti-malarial compound utilized and the particular therapeutic effect to be achieved, and (b) the limitations inherent in the art of compounding such an anti-malarial compound for the treatment of anti-inflammatory conditions in living subjects having a diseased condition in which bodily health is impaired as hereinbelow disclosed.

Therapeutic Rationale

The inventive methods, detailed below, may be applied by the clinician to treat a variety of inflammatory conditions. Inflammatory conditions typically involve activation of the immune system, usually via steps of antigen recognition and presentation and T-cell activation. Immune responses are promoted by chemotactic, proinflammatory mediators including leukotrienes, and cytokines and interleukins such as IL-1, Il-4 or TNF as well as effector cells such as neutrophils, macrophages or eosinophils. Antibodies, including allergic IgE class antibodies, may also participate which in turn may elicit mast cell activation and triggering responses. Granulomatous inflammation resulting from cell-mediated responses characterizes some inflammatory disease states. The anti-inflammatory agents of the present invention retard the progression of these biochemical processes described hereinabove.

Although the inventor does not wish to be bound by any theory of mechanism of the invention, it is believed that the therapeutic approach of the present invention effectively inhibits or attenuates at least one of the inflammation-related processes. The inhibition or attenuation of one or more of the underlying causative or exacerbating processes is effected by the anti-malarial agents that have anti-inflammatory effect, thus results in an effective-treatment of a variety of inflammatory conditions.

As noted previously, conventional therapies, i.e., systemic deliveries of anti-malarials, especially by oral administration, suffer from significant failings. For example, when HCQ is delivered through the conventional systemic routes, there is a significant delay in the onset of the anti-malarial action, due to active concentration of the therapeutic agent in certain organs, which are often not the target organ. Moreover, long-term high dose use has been shown to carry a risk of serious side effects, including retinal damage.

Nevertheless, it was thought heretofore that systemic delivery was necessary to achieve a therapeutic effect. Thus, like other anti-inflammatory pharmaceuticals, anti-malarial compounds have uniformly been prescribed systemically, typically by oral dosing.

The present invention is the first to demonstrate that targeted delivery of an anti-malarial compound to an internal organ, via mucosal, serosal, or synovial application, for example, is effective in treating inflammatory conditions. The inventor has found, unexpectedly, that localized delivery of anti-malarial compounds maintains or improves therapeutic value, while avoiding the problems associated with conventional treatment regimes.

Also unexpected is the inventor's demonstration that locally delivered anti-malarial compounds, such as HCQ, have potent anti-asthmatic effects, including anti-bronchospastic effect, effectively blocking early phase allergic response, and ablation of late-phase allergic response. Inhaled anti-malarial compounds, such as HCQ, are well tolerated as evidenced by the lack of increase in airway resistance after inhalation, demonstrating that the nebulized form is not a bronchial irritant and, hence, is suitable for administration via inhalation. Moreover, the local administration of the anti-malarial compounds significantly reduces and/or eliminates the toxic side-effects of these compounds which are manifested when given by systemic administration, such as by oral administration. The major toxicity of this class of pharmaceuticals when given systemically is related to the selective accumulation of the drug in the retina and subsequent binding of melanin which may lead to retinal photoreceptor damage. This may lead to retinal damage. Other side effects associated with hydroxychloroquine therapy include nausea, anorexia, diarrhea, pruritus, urticaria, increased skin pigmentation, exfoliative dermatitus, headache, and scotomata. By administering the antimalarial, such as HCQ locally, such by inhalation, less drug is required and therefore either the patient does not experience the aforementioned side effects or, if experienced, they are significantly less severe.

Relative to systemic administration, such as oral administration, the present invention has significant benefits over available oral or systemically administered routes, such as a more rapid accumulation of therapeutic amounts of compound in the tissue which is targeted, as well as a rapid onset of action, measured in days as opposed to months. Localized delivery results in reduced dosage requirements, both daily and cumulatively, and minimizes side effects.

The low-dose, targeted, and organ-oriented approach of the instant invention minimizes all the drawbacks of the systemic approach, such as increased cost for the medicine and inconvenience to the patients, resulting from prolonged and high dose usage.

The anti-malarial compounds of the invention, especially, aminoquinoline derivatives, are, without wishing to be bound, believed to be particularly effective because they are multi-factorial inhibitors, blocking both humoral and cell-mediated/delayed response immune systems. Anti-malarial compounds, such as aminoquinoline derivatives, appear to exert their pharmacologic effects due to several underlying properties. For example, see MacKenzie, 1983*, Am J Medicine* 75:1A:5–10; Fox, 1993*, Sem. Arthritis Rheumatism* 23:82–91.

These properties seem to result from the unique effect on membranes of compounds in this group. Without wishing to be bound, it is believed that anti-malarial compounds, such as aminoquinoline derivatives, are able to elevate intravesical pH by intracellularly concentrating in acidic cytoplasmic vesicles in a variety of immune function cells. Since several processes critical for the generation of immune response depends on neutral or acidic pH environments, this action inhibits cellular functions in mature cells such as lymphocytes, monocytes, neutrophils and macrophages which depend on an active lysosomal system.

Interference with vesical fusion decreases secretion and release of intracellular products, such as immunoglobins including IgE (allergic antibody), interleukins and cytokines used in signaling and augmenting immune responses (e.g., IL-1, IL-6, TNF-α, ICAM-1, IL-4), exocytosis of lysosomal products such as superoxides in neutrophils and macrophages. Similarly, such interference also decreases efficiency of phagolysosomal system by inhibiting production of superoxides in neutrophils. Furthermore, increases of lysosomal pH interfere with lysosomal acid hydrolases. As a consequence of these actions, antigen processing is inhibited.

Furthermore, the interference with vesical fusion causes depletion of surface receptors due to sequestion of plasma membranes in stabilized intercellular vesicles. This leads to depletion of cell surface markers necessary for antigen presentation, immune recognition, and cellular responsiveness. As a result, T-cell activation is inhibited, and interleukin responses antagonized. For example, HCQ blocks the actions of IL-4 (Seggev J Immunol 150:62A), an interleukin both critical for the recruitment of eosinophils, a primary effector cell in asthmatic inflammation, and for the generation of IgE allergic antibody.

The depletion of cell surface markers has been reported to reduce the transmission of a number of viruses including rhinovirus and adenovirus. In part, this may be due to known reduction of membrane receptors, such as ICAM-1, which are critical for viral uptake. Interference with the phagolysosomal system may help explain an observed decrease in viral replication for other viruses including HIV and influenza.

Cumulatively, the result of anti-malarial compound, including aminoquinoline derivative, inhibition of antigen presentation and T-cell activation is a reduction in delayed hypersensitivity (cell-mediated) responses, modulation of humoral responses, decreases in viral uptake and replication, modulation and/or suppression of early and late phase allergic response, and inhibition of inflammatory effector cell function. Finally, derivatives of anti-malarials, including aminoquinolines, are reported to block viral replication and transmission (for example, of rhinovirus and adenovirus) and to have anti-brochospastic effects.

The inventor has found that each of the effects noted above can be accomplished via localized delivery, for example, by application of the anti-malarial compounds to musocal, serosal, or synovial application and uptake.

In sum, anti-malarial compounds such as the aminoquinoline derivatives have beneficial effects with respect to a wide range of inflammatory diseases, including granulomatous, neutrophil, mast cell, eosinophil, basophil, and macrophage-mediated inflammation as well as humoral antibody mediated-inflammation. The ability of these multifactorial agents to modify a wide range of local responses supports their use of localized delivery to sclera, nasal or oral mucosa, bronchial epithelium, or lower intestine and sigmoid colon, because these inflammatory manifestations all have in common the participation of immune cells which generate a local inflammatory response, despite other differences among these inflammatory conditions. For each of these illnesses, localized delivery has the same advantages, including more rapid onset of action at less risk due to lower cumulative and daily doses.

Therapeutic Methodology

In accordance with the present invention, a therapeutic composition as described above, typically is applied to patients suffering from an inflammatory condition. Inflammatory conditions usually are characterized by an activation of the immune system, such as T-cell activation. Such activation often is mediated by effector cells, such as neutrophils, macrophages or eosinophils, and may be promoted by specific mediators such as IL-1, Il-4 or TNF or allergic antibodies. Some inflammatory conditions involve cell-mediated granulomatous inflammation.

Thus, a patient in this context often will suffer from a disorder characterized by one or more of the foregoing signs of an inflammatory condition. By the same token, the present invention entails localized administration, to a patient in need, of an anti-malarial compound, formulated along the lines detailed above, in an amount that alleviates or ameliorates a symptom or the underlying pathology of an inflammatory condition ("an effective amount" or "anti-inflammatory effective amount").

Specific examples of inflammatory conditions treatable according to the invention include, but are not limited to, scleritis; epi-scleritis; allergic conjunctivitis; pulmonary inflammatory diseases, particularly asthma, chronic obstructive pulmonary disease (COPD), allergic bronchopulmonary aspergillosis (ABPA), and sarcoidosis; procto-sigmoiditis; allergic rhinitis; arthritis; tendonitis; apthous stomatitis; and inflammatory bowel disease.

The compound may be administered by any suitable means, as described hereinabove depending on the condition being treated. For example, in treating ocular diseases, such as scleritis and epi-scleritis or allergic conjunctivitis, the compound may be administered as a topical ophthalmic preparation. On the other hand, it may be compounded as nasal spray or mist for inhalation in treating allergic rhinitis. Treating apthous stomatitis advantageously employs an oral paste. Parenteral injections are suitable for the localized treatment of arthritis or tendonitis. Procto-sigmoiditis, and the like, will usually be treated with an appropriately formulated retention enema. Asthmatic and non-asthmatic pulmonary conditions, such as COPD, and ABPA, may be and preferably are treated by inhalation of a suitable composition.

As used herein, the plural signifies the singular and vice-versa.

Moreover, in the chemical formula described hereinabove, if not specifically drawn, it is to be understood that if a central atom does not have all the valences, the remaining bonds are to hydrogen atoms.

The following examples are given to illustrate the present invention. It should be understood, however, that the invention is not to be limited to the specific conditions or details described in these examples. In addition, throughout the specification, any and all references to publicly available documents are specifically incorporated by reference.

Animal Studies of the Effect of Nebulized HCQ on Asthma

Using a well established animal model of asthma employing Ascaris-sensitized sheep (Abraham, et al., *Am. J. Respir. Crit. Care Med.*, 1997, 156:696–703), the contents of which are incorporated by reference, the inventor completed animal experiments investigating the effect of nebulized HCQ on early and late allergic asthmatic responses to antigen challenge. These studies confirm that targeted and localized delivery of HCQ has potent anti-asthmatic effects. In addition, quite unexpectedly, local delivery, in this case administered via nebulized aerosol, resulted in more rapid onset of drug effect than in oral administration and at significantly lower dosage levels, both daily and cumulatively.

Inhaled HCQ partially blocks immediate allergic-mediated bronchostrictive responses, virtually eliminates late-phase responses which occur on four to 12 hours post-antigen challenge, and moreover, shows continued effect at blocking the bronchial hyperresponsiveness even twenty-four hours later after local administration of the anti-malarial compound. Because late phase allergic inflammatory responses is the most complete representation of the bronchial inflammation that characterizes asthma, these findings underline the potent local anti-inflammatory capabilities of anti-malarial compounds, e.g., aminoquinolines like HCQ, which do not rely on its systemic effects, but rather are generated in an organ-specific manner (in this case the bronchial airways) when delivered by inhalation.

METHODS FOR EXAMPLES 1–2

All procedures were approved by the Mount Sinai Medical Center Animal Research Committee, which is responsible for assuring the humane care and use of experimental animals. The sheep used for this study had previously been shown to develop early and late airway responses and airway hyperresponsiveness to inhaled carbachol following inhalation challenge with *Ascaris suum* antigen.

Measurement of Airway Mechanics: The unsedated sheep were restrained in a cart in the prone position with their heads immobilized. After topical anesthesia of the nasal passages with 2% lidocaine solution, a balloon catheter was advanced through one nostril into the lower esophagus. The animals were incubated with a cuffed endotracheal tube through the other nostril using a flexible fiberoptic bronchoscope as a guide. (The cuff of the endotracheal tube was inflated only for the measurement of airway mechanics and during aerosol challenges to prevent undue discomfort. This procedure has no effect on airway mechanics). Pleural pressure was estimated with the esophageal balloon catheter (filled with one ml of air) which was positioned 5–10 cm from the gastroesophageal junction. In this position, the end expiratory pleural pressure ranged between −2 and −5 cm $H_2O$. Once the balloon was placed, it was secured so that it remained in position for the duration of the experiment. Lateral pressure in the trachea was measured with a sidehole catheter (inner dimension, 2.5 mm) advanced through and positioned distal to the tip of the endotracheal tube. Transpulmonary pressure, the difference between tracheal and pleural pressure, was measured with a differential pressure transducer catheter system. For the measurement of pulmonary resistance ($R_L$), the proximal end of the endotracheal tube was connected to a pneumotachograph (Fleisch No. 1; Dyna Sciences, Inc., Blue Bell, Pa.). The transpulmonary pressure and flow signals were recorded on a multichannel physiologic recorder, which was linked to an 80–386 DOS Personal Computer (CCI Inc., Miami, Fla.) for on-line calculation of mean pulmonary flow resistance (RL) by dividing the change in transpulmonary pressure by the change in flow at mid-tidal volume ($V_T$) (obtained by digital integration). The mean of at least five breaths, free of swallowing artifact, was used to obtain $R_L$ in cm $H_2O/L/s$. Immediately after the measurement of $R_L$, thoracic gas volume (Vtg) was measured in a constant-volume body plethysmograph to obtain specific lung resistance ($SR_L = R_L \times V_{tg}$) in L×cm $H_2O/L/s$.

Aerosol Delivery Systems: Aerosols of *Ascaris suum* extract (diluted 20:1 with phosphate buffered saline; 82,000 PNU/ml) were generated using a disposable medical nebulizer (Raindrop®, Puritan Bennett), which produces an aerosol with a mass median aerodynamic diameter of 3.2 μm (geometric standard deviation, 1.9) as determined by a 7 stage Andersen cascade impactor. The output from the nebulizer was directed into a plastic T-piece, one end of which was connected to the inspiratory port of a Harvard respirator. To better control aerosol delivery, a dosimeter consisting of a solenoid valve and a source of compressed air (20 psi) was activated at the beginning of the inspiratory cycle of the Harvard respirator system for 1 second. The aerosol was delivered at a tidal volume of 500 ml and a rate of 20 breaths per minute for 20 minutes. Each sheep was challenged with an equivalent dose of antigen (400 breaths) in the control and drug trials. Carbachol aerosols were also generated with this same nebulizer system.

Dose Response Curves to Inhaled Carbachol: For the carbachol dose response curves, measurements of $SR_L$ were repeated immediately after inhalation of buffer and after each administration of 10 breaths of increasing concentrations of carbachol solution (0.25%, 0.5%, 1.0%, 2.0% and 4.0% w/v). To assess airway responsiveness, the cumulative carbachol dose in breath units (BU) that increased $SR_L$ 400% over the post-buffer value (i.e. $PC_{400}$) was calculated from the dose response curve. One breath unit was defined as one breath of a 1% w/v carbachol solution.

Bronchial Biopsies

Bronchial biopsies were done before the initiation of treatment and 24 h after antigen challenge. Pre- and postchallenge biopsy specimens were obtained from opposite lungs, and at least three specimens were obtained from each lung at each time point. Biopsy specimens were fixed in 10% buffered formalin and processed routinely for puraffin embedding. Tissue sections (4 μm) were stained with Giemsa, using the microwave method described in Churukian, 1995, *J. Histotech.*, 18:319–322, the content of which are incorporated by reference. This technique gives more uniform staining and better contrast between nuclei and cytoplasm. Parallel sections were stained with toluidine blue for identification of meta-chromatic-staining cells (most cells/basophils). Slides were examined with a BH2 light microscopic (Olympus Corp., Tokyo, Japan) equipped with differential interference contrast optics, using a calibrated eye piece grid (10×10), which covered 1,600 $\mu m^2$ with a X40 objective. The number and distribution of inflammatory cells (polymorphonuclear leukocytes [PMN], lymphocytes, eosinophils, and mast cells/basophils) was assessed in bronchial epithelium and lamina propria. A minimum of five fields from each biopsy were examined, the number of cells for each cell type were averaged for the five fields, and the results were expressed as number of cells/grid.

Agents

*Ascaris suum* extract (Great Diagnostics, Lenor, N.C.) was diluted with PBS to a concentration of 82,000 protein nitrogen units/ml and delivered as an aerosol (20 breaths/min×20 min). This crude preparation has an endotoxin level of 50 Eu/ml, which does not have a pulmonary effect in sheep. Carbamylcholine (Carbachol; Sigma Chemical Co., St. Louis, Mo.) was dissolved in buffered saline at concentrations of 0.25, 0.50, 1.0, 2.0 and 4.0% wt/vol and delivered as an aerosol.

EXAMPLE 1

At 3 to 4 days before treatment was begun, baseline airway responsiveness, to aerosol carbachol (i.e., $PC_{400}$) was determined and a baseline bronchial biopsy performed. Then at 4 days before antigen challenge, the asthmatic sheep began treatment with 30 mg an average of 0.78 mg/kg HCQ (30 mg/animal, 30 mg in 5 cc Normal Saline, given as aerosol). The animals were treated two times a day for 3 days and then, on the fourth day, at 0.5 hours before antigen challenge and again at 4 hours after challenge. On the antigen-challenge day, $SR_L$ was measured and the animals were than treated with HCQ designated compound. $SR_L$ was remeasured 0.5 h after treatment (just before challenge) and the animals were then challenged with antigen. $SR_L$ was then remeasured immediately after.

The results were compared to those obtained with the sheep to which PBS were administered in lieu of the drug and challenged in the same fashion. The results are tabulated in Table 1 and graphically represented in FIG. 1.

The results indicate that application of HCQ in aerosolized form does not cause any major irritant effects. For example, specific resistance, obtained pre- and immediately following HCQ application, showed no change following antigen challenge (see FIG. 1 and Table 1). Specific resistance rose an average of 232% in the control group but only 95% in the treated group. This effect is similar to that seen with other available anti-asthmatic drugs, such as inhaled budesonide (Abraham, W. M., Late phase responses in the sheep, in Airways smooth muscle: modeling the asthmatic responses in vivo, ed., D. Raeburn and M A Giembycz, Birkauser, Boston).

EXAMPLE 2

Figure 2:
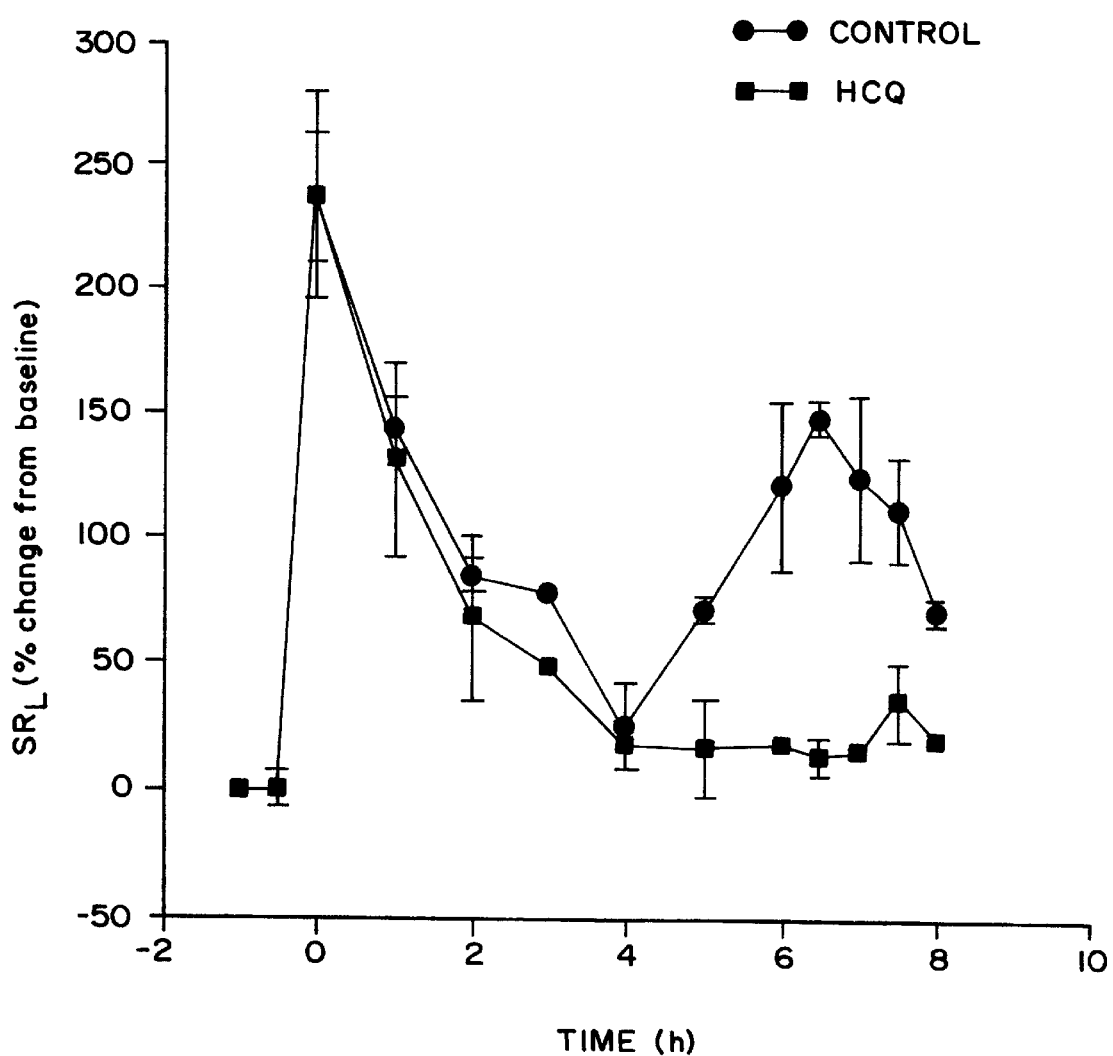

In a second experiment, the procedure of Example 1 was followed except the animals received a dosage of an average of 40 mg b.i.d. (2 mg/kg/day) of HCQ for 3 days. On the fourth day, they received an additional treatment one-half hour prior to antigen challenge. While acute reactions were not inhibited, late phase asthmatic reactions were virtually completely blocked in the drug-treatment group. Specific resistance in the control group peaked at an increase of a mean of 148% at 6.5 hours, compared to a mean increase of only 14% in the drug-treated group. See FIG. 2 and Table 2.

Figure 3:
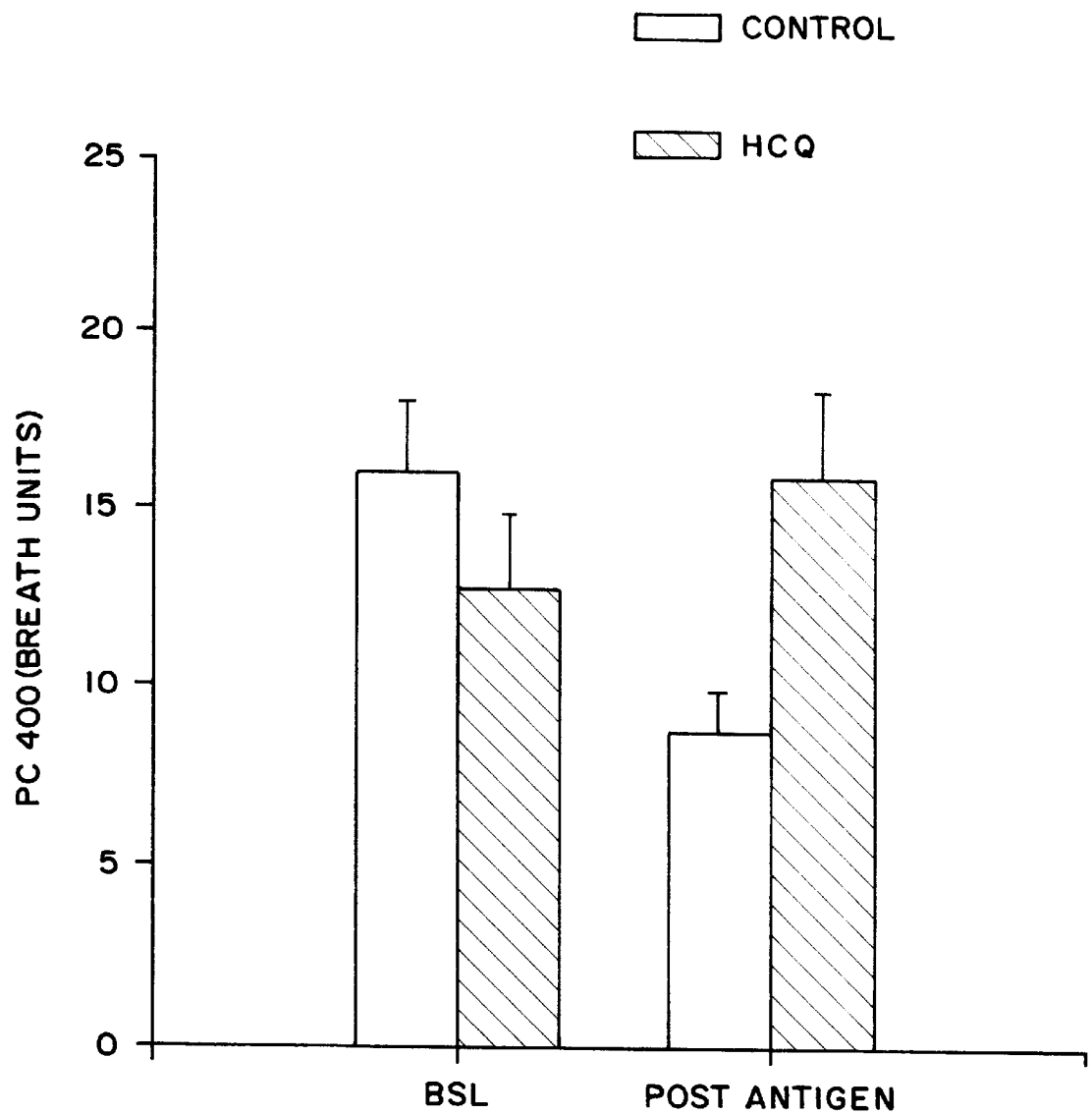

Underlining the potent effect of the HCQ treatment, a 24 hour post-antigen challenge carbachol reactivity (PC 400 as measured in breath units) increased in the control group by 50% as anticipated, but actually fell in the treatment group from 12.74 to 15.82 units (see FIG. 3).

TABLE 1

Specific resistance following antigen challenge (Example 1)

| Sheep No. | BSLN. Srl | p-pl/dg Srl | p-pl/dg % | p-pl/dg Srl | p-pl/dg % | P-ASC Srl | P-ASC % | +1 HR Srl | +1 HR % | +2 HRS Srl | +2 HRS % | +3 HRS Srl |
|---|---|---|---|---|---|---|---|---|---|---|---|---|
| CONTROL TRIAL: (immediate) (just before Ag) | | | | | | | | | | | | |
| 933 | 0.94 | 0.94 | 0% | 0.94 | 0% | 3.4 | 262% | 1.14 | 21% | 1.1 | 17% | |
| 1483 | 1.17 | 1.17 | 0% | 1.17 | 0% | 3.54 | 203% | 1.19 | 2% | 1.15 | 22% | |

TABLE 1-continued

Specific resistance following antigen challenge
(Example 1)

| Sheep No. | BSLN. Srl | p-pl/dg Srl | p-pl/dg % | p-pl/dg Srl | p-pl/dg % | P-ASC Srl | P-ASC % | +1 HR Srl | +1 HR % | +2 HRS Srl | +2 HRS % | +3 HRS Srl |
|---|---|---|---|---|---|---|---|---|---|---|---|---|
| 1530 | 1.05 | 1.05 | 0% | 1.05 | 0% | 2.5 | 138% | 1.54 | 47% | 1.02 | -3% | |
| Mean : | 1.06 | 1.06 | 0% | 1.06 | 0% | 3.47 | 232% | 1.17 | 11% | 1.13 | 20% | 0.00 |
| SE : | 0.12 | 0.12 | 0% | 0.12 | 0% | 0.07 | 30% | 0.03 | 10% | 0.02 | 2% | 0.00 |
| COMPOUND TRIAL | | | | | | | | | | | | |
| 933 | 1.02 | 1.20 | 18% | 1.11 | 9% | 2.45 | 140% | 1.35 | 32% | 1.13 | 11% | |
| 1483 | 1.00 | 1.02 | 2% | 0.95 | -5% | 1.49 | 49% | 1.43 | 43% | 1.74 | 74% | |
| 1530 | 1.15 | 1.37 | 19% | 1.13 | -2% | 3.32 | 189% | 1.49 | 30% | 1.2 | 4% | |
| Mean : | 1.01 | 1.11 | 10% | 1.03 | 2% | 1.97 | 95% | 1.39 | 38% | 1.44 | 42% | 0.00 |
| SE : | 0.01 | 0.09 | 8% | 0.08 | 7% | 0.48 | 46% | 0.04 | 5% | 0.31 | 32% | 0.00 |

TABLE 2

Specific resistance following antigen challenge
(Example 2)

| Sheep No. | BSLN. Srl | p-pl/dg Srl | p-pl/dg % | p-pl/dg Srl | p-pl/dg % | P-ASC Srl | P-ASC % | +1 HR Srl | +1 HR % | +2 HRS Srl | +2 HRS % | +3 HRS Srl |
|---|---|---|---|---|---|---|---|---|---|---|---|---|
| CONTROL TRIAL: (immediate) (just before Ag) | | | | | | | | | | | | |
| 1125 | 1.04 | 1.04 | 0% | 1.04 | 0% | 3.24 | 212% | 2.41 | 132% | 2.1 | 92% | 1.89 |
| 1534 | 1.11 | 1.11 | 0% | 1.11 | 0% | 4.03 | 263% | 2.85 | 157% | 1.99 | 79% | 1.96 |
| Mean : | 1.08 | 1.08 | 0% | 1.08 | 0% | 3.64 | 237% | 2.63 | 144% | 2.00 | 86% | 1.93 |
| SE : | 0.04 | 0.04 | 0% | 0.04 | 0% | 0.40 | 26% | 0.22 | 13% | 0.01 | 7% | 0.04 |
| COMPOUND TRIAL | | | | | | | | | | | | |
| 1125 | 1.02 | 1.15 | 13% | 0.96 | -6% | 3.02 | 196% | 2.76 | 171% | 2.06 | 102% | 1.57 |
| 1534 | 1.09 | 1.01 | -7% | 1.17 | 7% | 4.14 | 280% | 2.10 | 93% | 1.48 | 36% | 1.59 |
| Mean : | 1.06 | 1.08 | 3% | 1.07 | 1% | 3.58 | 238% | 2.43 | 132% | 1.74 | 69% | 1.58 |
| SE : | 0.04 | 0.07 | 10% | 0.11 | 7% | 0.56 | 42% | 0.33 | 39% | 0.29 | 33% | 0.01 |

| Sheep No. | +3 HRS % | +4 HRS Srl | +4 HRS % | +5 HRS Srl | +5 HRS % | +6 HRS Srl | +6 HRS % | +6 HRS Srl | +6 HRS % | +7 HRS Srl | +7 HRS % |
|---|---|---|---|---|---|---|---|---|---|---|---|
| CONTROL TRIAL: (immediate) (just before Ag) | | | | | | | | | | | | |
| 1125 | 82% | 1.14 | 10% | 1.73 | 66% | 2.65 | 155% | 2.65 | 155% | 2.68 | 158% |
| 1534 | 77% | 1.59 | 43% | 1.95 | 76% | 2.08 | 87% | 2.68 | 141% | 2.12 | 91% |
| Mean : | 79% | 1.37 | 26% | 1.84 | 71% | 2.37 | 121% | 2.67 | 148% | 2.40 | 124% |
| SE : | 3% | 0.23 | 17% | 0.11 | 5% | 0.28 | 34% | 0.02 | 7% | 0.28 | 33% |
| COMPOUND TRIAL | | | | | | | | | | | |
| 1125 | 54% | 1.12 | 10% | 1.39 | 36% | 1.22 | 20% | 1.10 | 8% | 1.22 | 20% |
| 1534 | 46% | 1.39 | 28% | 1.07 | -2% | 1.26 | 16% | 1.32 | 21% | 1.23 | 13% |
| Mean : | 50% | 1.26 | 19% | 1.23 | 17% | 1.24 | 18% | 1.21 | 14% | 1.23 | 16% |
| SE : | 4% | 0.13 | 9% | 0.16 | 19% | 0.02 | 2% | 0.11 | 7% | 0.01 | 3% |

| SHEEP No. | +7.5 HRS Srl | +7.5 HRS % | +8 HRS Srl | +8 HRS % | ORC #1 BSLN. | ORC #2 (24 P-Ag.) |
|---|---|---|---|---|---|---|
| CONTROL TRIAL: (immediate) (just before Ag) | | | | | | |
| 1125 | 2.42 | 133% | 1.71 | 64% | 18.04 | 9.76 |
| 1534 | 2.11 | 90% | 1.94 | 75% | 13.98 | 7.48 |
| Mean : | 2.26 | 111% | 1.83% | 70% | 16.01 | 8.62 |
| SE : | 0.16 | 21% | 0.12 | 5% | 2.03 | 1.14 |
| COMPOUND TRIAL | | | | | | |
| 1125 | 1.53 | 50% | 1.24 | 22% | 10.65 | 15.86 |
| 1534 | 1.30 | 19% | 1.29 | 18% | 14.83 | 15.77 |
| Mean : | 1.42 | 35% | 1.27 | 20% | 12.74 | 15.82 |
| SE : | 0.12 | 15% | 0.03 | 2% | 2.09 | 0.04 |

METHODS OF EXAMPLE 3

All procedures were approved by the Mount Sinai Medical Center Animal Research Committee, which is responsible for assuring the humane care and use of experimental animals. The sheep used for this study had previously been shown to develop early and late airway responses and airway hyperresponsiveness to inhaled carbachol following inhalation challenge with *Ascaris suum* antigen. During the chronic treatment trail, venous blood samples were obtained from the external jugular vein for the determination of plasma compound concentrations. Samples were obtained as baseline (pre-dosing), and, then, before dosing on days 8, 15, 22, 29 and after dosing had stopped on day 43.

Measurement of Airway Mechanics: The unsedated sheep were restrained in a cart in the prone position with their heads immobilized. After topical anesthesia of the nasal passages with 2% lidocaine solution, a balloon catheter was advanced through one nostril into the lower esophagus. The animals were incubated with a cuffed endotracheal tube through the other nostril using a flexible fiberoptic bronchoscope as a guide. (The cuff of the endotracheal tube was inflated only for the measurement of airway mechanics and during aerosol challenges to prevent undue discomfort. This procedure has no effect on airway mechanics). Pleural pressure was estimated with the esophageal balloon catheter (filled with one ml of air) which was positioned 5–10 cm from the gastroesophageal junction. In this position, the end expiratory pleural pressure ranged between −2 and −5 cm $H_2O$. Once the balloon was placed, it was secured so that it remained in position for the duration of the experiment. Lateral pressure in the trachea was measured with a sidehole catheter (inner dimension, 2.5 mm) advanced through and positioned distal to the tip of the endotracheal tube. Transpulmonary pressure, the difference between tracheal and pleural pressure, was measured with a differential pressure transducer catheter system. For the measurement of pulmonary resistance ($R_L$), the proximal end of the endotracheal tube was connected to a pneumotachograph. The signals of flow and transpulmonary pressure were recorded on a n oscilloscope recorder which was linked to a computer for on-line calculation of $R_L$ from transpulmonary pressure, respiratory volume (obtained by digital integration) and flow. Analysis of 5–10 breaths were used for the determination of $R_L$. Immediately after the measurement of $R_L$, thoracic gas volume ($V_{tg}$) was measured in a constant volume body plethysmograph to obtain specific lung resistance ($SR_L=R_L \cdot V_{tg}$) in cm $H_2O \cdot sec^{-1}$.

Aerosol Delivery Systems: Aerosols of Ascaris suum extract (diluted 20:1 with phosphate buffered saline; 82,000 PNU/ml) were generated using a disposable medical nebulizer (Raindrop®, Puritan Bennett), which produces an aerosol with a mass median aerodynamic diameter of 3.2 $\mu$m (geometric standard deviation, 1.9) as determined by a 7 stage Andersen cascade impactor. The output from the nebulizer was directed into a plastic T-piece, one end of which was connected to the inspiratory port of a Harvard respirator. To better control aerosol delivery, a dosimeter consisting of a solenoid valve and a source of compressed air (20 psi) was activated at the beginning of the inspiratory cycle of the Harvard respirator system for 1 second. The aerosol was delivered at a tidal volume of 500 ml and a rate of 20 breaths per minute for 20 minutes. Each sheep was challenged with an equivalent dose of antigen (400 breaths) in the control and drug trials. Carbachol aerosols were also generated with this same nebulizer system.

Dose Response Curves to Inhaled Carbachol: For the carbachol dose response curves, measurements of $SR_L$ were repeated immediately after inhalation of buffer and after each administration of 10 breaths of increasing concentrations of carbachol solution (0.25%, 0.5%, 1.0%, 2.0% and 4.0% w/v). To assess airway responsiveness, the cumulative carbachol dose in breath units (BU) that increased $SR_L$ 400% over the post-buffer value (i.e. $PC_{400}$) was calculated from the dose response curve. One breath unit was defined as one breath of a 1% w/v carbachol solution.

EXPERIMENTAL PROTOCOL

The same basic protocol was used for all studies in Example 3. This basic protocol consisted of first obtaining baseline dose response curves to aerosol carbachol 1–3 days prior to antigen challenge. Then, on the day of antigen challenge, values of specific lung resistance ($SR_L$) were measured at baseline and, then, 30 min after drug or vehicle (0.9% saline) treatment. The animals were, then, challenged with Ascaris suum antigen and $SR_L$ was remeasured immediately after challenge, hourly from 1–6 h after challenge and on the half-hour from 6½–8 h after challenge. Measurements of $SR_L$ were obtained 24 h after challenge followed by the 24 h post challenge dose response curve.

Studies differed in time of treatment, treatment dose or route of administration. In the first series, animals were treated with 1 mg/kg HCQ (dissolved in 5 ml 0.9% saline) by aerosol twice a day for 3 days and, then, on again on the $4^{th}$ (antigen challenge day) 30 min before and 8 h after antigen challenge. A second control challenge was done 2 weeks after the drug trial to insure that the 4 day treatment regimen had no carry-over effect. In the second series, this same treatment regimen was used except the sheep received HCQ, p.o.(1 mg/kg in 10 ml 0.9% saline). A second control challenge was done 2 weeks after the drug trial to insure that the 4 day treatment regimen had no carry-over effect. In the third series of studies, sheep were treated with 2 mg/kg HCQ (dissolved in 5 ml 0.9% saline) by aerosol, once a day for 3 days and, then, on again on the $_4$th (antigen challenge day) 30 min before antigen challenge. A second control challenge was done 2 weeks after the drug trial to insure that the 4 day treatment regimen had no carry-over effect. In the fourth series, the 4 day single treatment protocol was used, and the sheep used in the third series of experiments were treated with 0.2 mg/kg HCQ aerosol and 0.6 mg/kg HCQ aerosol (both dissolved in 5 ml 0.9% saline). Challenges were separated by 2 weeks. In the fifth series, sheep were challenged with 2 mg/kg HCQ aerosol (dissolved in 5 ml 0.9% saline), once a day for 14 days. On the $15^{th}$ day, the animals were treated and 30 min later, challenged with antigen. On the following day, after determining the post challenge $PC_{400}$, the animals resumed treatment for another 14 days, after which, they were challenged with antigen (day 29). The animals were then left untreated for 14 days, after which an antigen challenge was conducted (day 43) and, then, this procedure was repeated after another 2 weeks (day 57).

STATISTICAL ANALYSIS

For each series, a repeated measures analysis of variance was performed to see if there were overall differences between the historical control the drug trial and the 2 week follow-up control or, in the case of experiments described in series 4 and 5, amongst the doses and different times, respectively. If a significant overall effect was found, then a two-tailed paired t-test were used to assess pairwise differences. The variables assessed were the peak early airway response (maximum increase in $SR_L$ 0–4 h after challenge), peak late airway response (maximum increase in $SR_L$ between 5–8 h after antigen challenge, irrespective of when this increase occurred for each sheep in each trial) and on the ratio of post challenge $PC_{400}$ to pre challenge $PC_{400}$. (Note: a ratio close to 1 indicates no airway hyperresponsiveness, whereas, a ratio close to 0.5 indicates the development of airway hyperresponsiveness.). Peak responses were used because they are the most conservative estimate of the overall effect. Values in the text and figures are mean±se for 3 sheep. Statistical analysis of these variables is reported in Table 3.

RESULTS 1 mg/kg HCQ Aerosol Twice a Day for 4 Days.

Figure 4A:
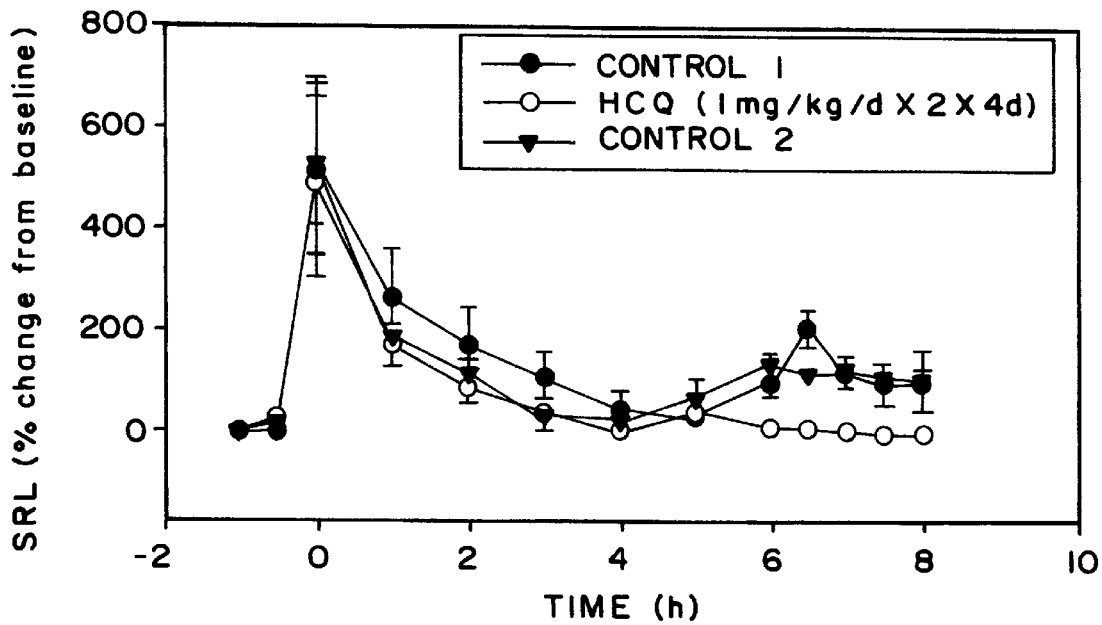
Figure 4B:
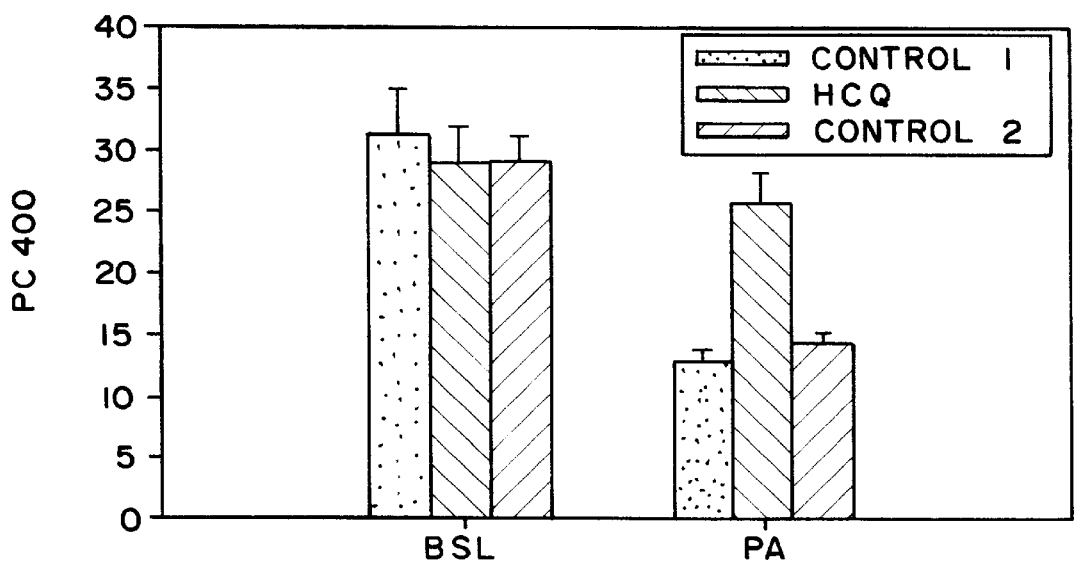

FIG. 4A illustrates the time course of the antigen-induced responses and FIG. 4B the effects on airway responsiveness in the three sheep treated with HCQ aerosol. There was no effect on the early airway response (EAR), however, HCQ aerosol blocked the late airway response (LAR) to allergen in these animals (ANOVA, P<0.001). Consistent with the protection against the late response was the protection against the airway hyperresponsiveness (AHR, ANOVA, P=0.011). Note that 2 weeks after treatment was stopped, the animals responded normally to allergen.

1 mg/kg HCQ, p.o. Twice a Day for 4 Days.

Figure 5A:
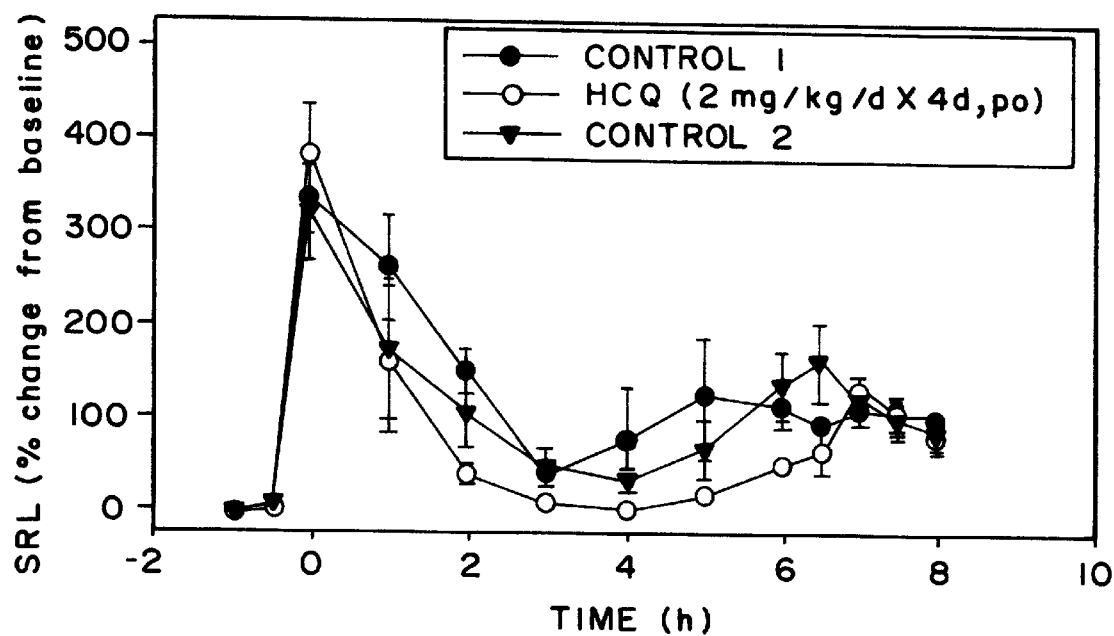
Figure 5B:
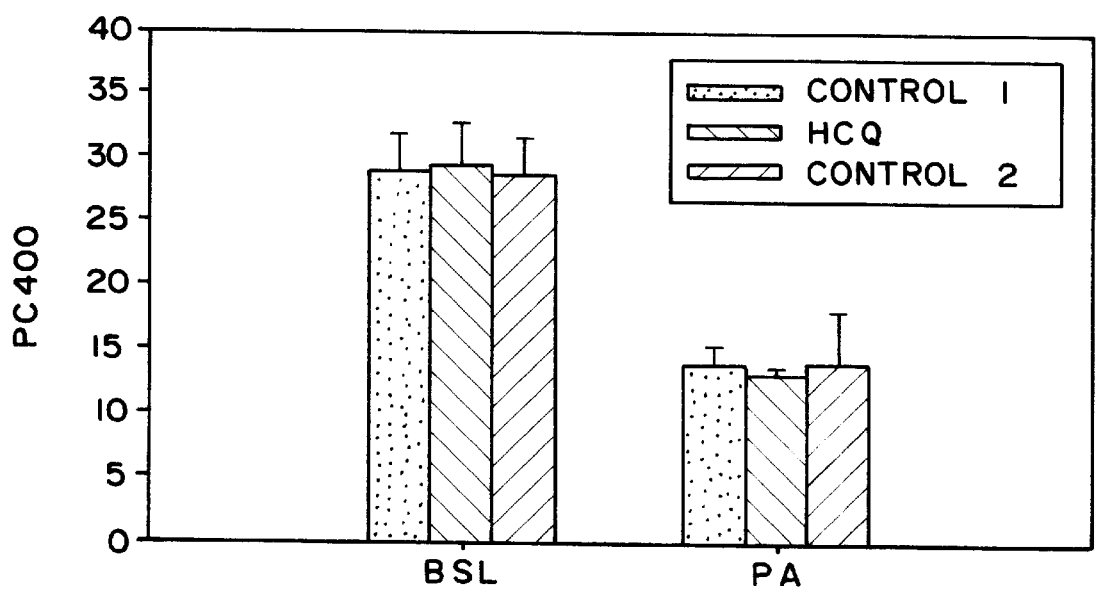

FIG. 5A illustrates the time course of the antigen-induced responses and FIG. 5B the effects on airway responsiveness in the three sheep treated with oral HCQ. Unlike when given by inhalation, oral treatment did not protect against the antigen-induced EAR, LAR or AHR.

Thus, the procedures in Series 1 and 2 and the data in FIGS. 4A, 4B, as compared to the data in FIGS. 5A and 5B show that local administration of HCQ greatly enhances the efficacy of the HCQ relative to systemic administration thereof, such as by oral administration.

2 mg/kg HCQ Aerosol Once a Day for 4 Days.

Figure 6A:
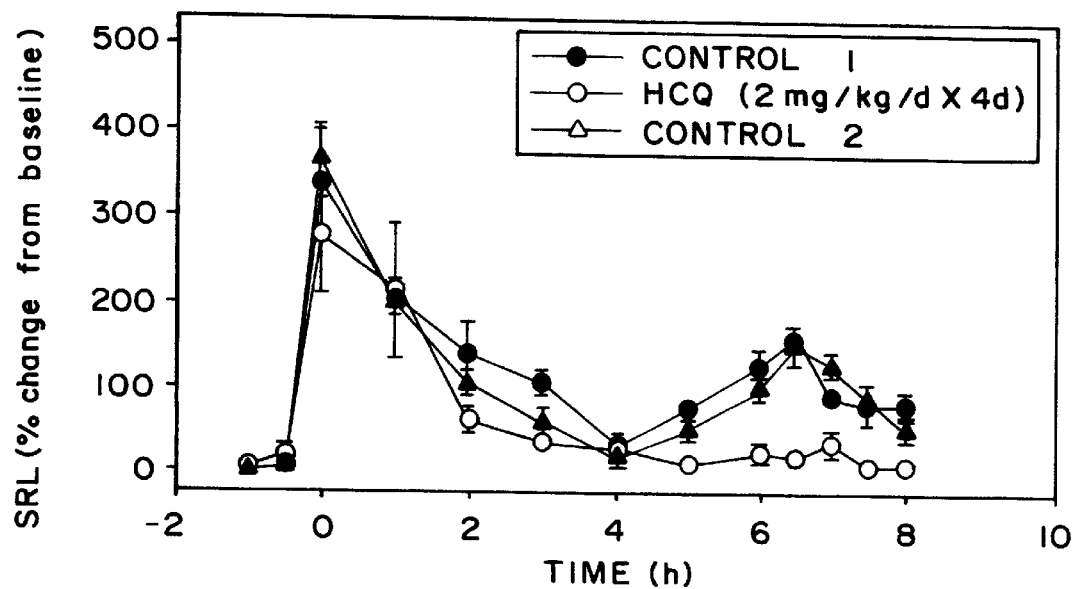
Figure 6B:
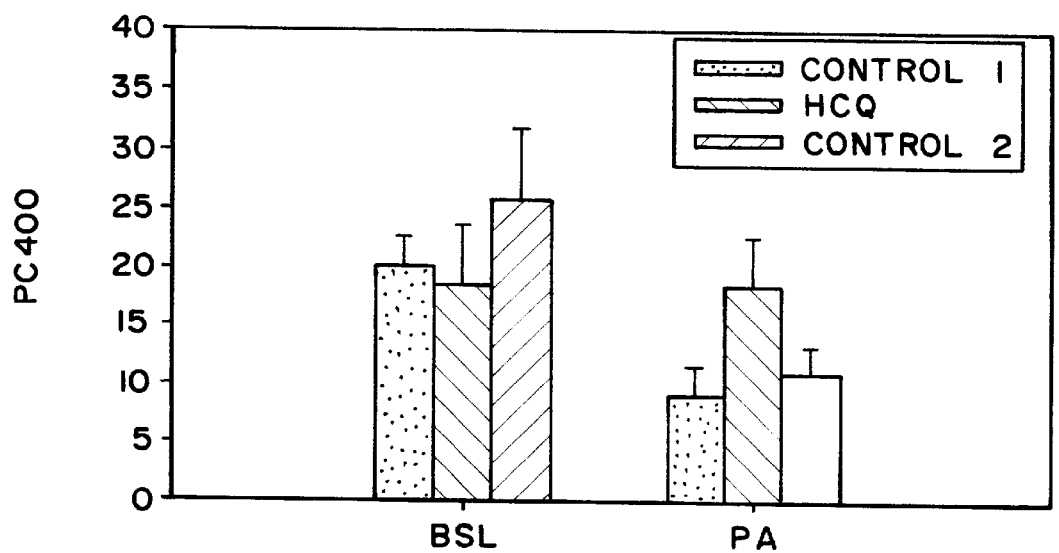

FIG. 6A illustrates the time course of the antigen-induced responses and FIG. 6B the effects on airway responsiveness in the three sheep treated once a day with HCQ aerosol. There was no effect on the EAR, however, HCQ aerosol blocked the LAR to allergen in these animals (ANOVA, P=0.001). Consistent with the protection against the late response was the protection against the antigen-induced AHR (ANOVA, P=0.026). Note that, 2 weeks after treatment was stopped, the animals responded normally to allergen. This shows that dosing by inhalation may be limited to once a day formulation.

Dose Response to Aerosol HCQ.

Figure 7A:
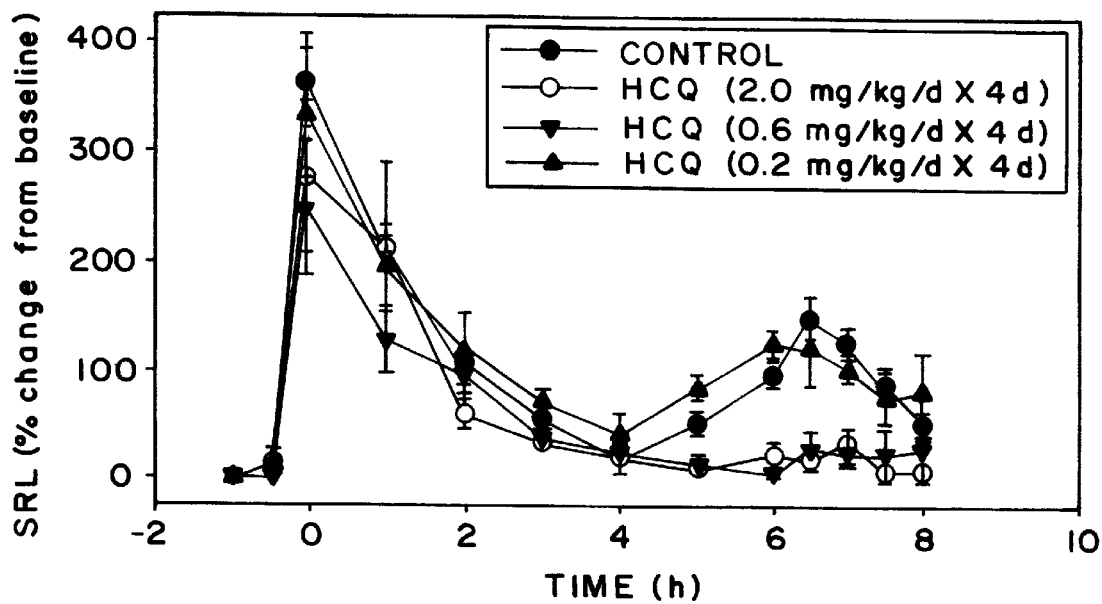
Figure 7B:
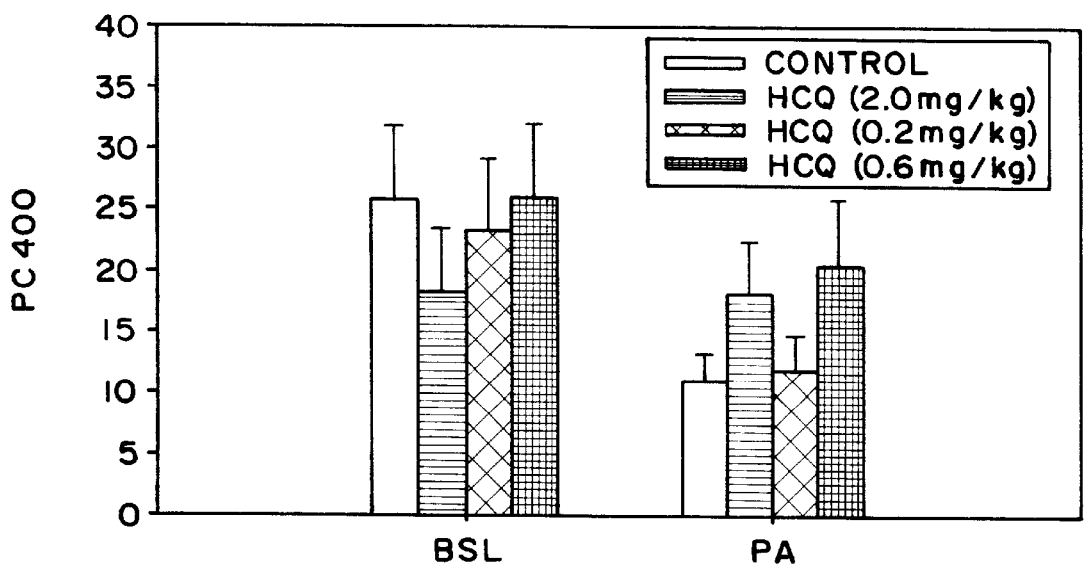
Figure 8:
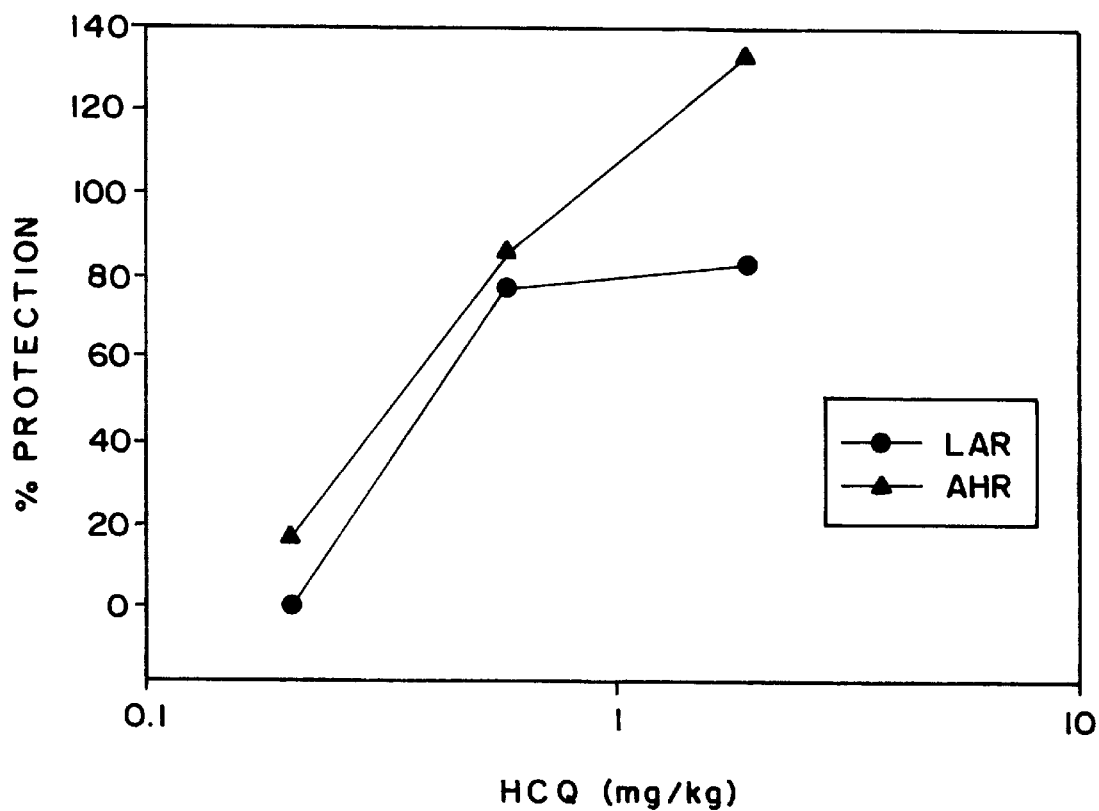

FIG. 7A illustrates the time course of the antigen-induced responses and FIG. 7B the effects on airway responsiveness in the three sheep treated with different doses of HCQ aerosol. There was no effect on the EAR, however, HCQ aerosol blocked the LAR to allergen in these animals (ANOVA, P=0.007). Consistent with the protection against the late response was the protection against the antigen-induced AHR (ANOVA, P=0.011). Overall, 0.6 mg/kg had significant protective effects in this trial. To get a better estimate of the dose-response relationship, the average LAR (between 5–8 h) for each dose was calculated, and this value was used to determine a mean percent protection. Likewise, the mean values for AHR shown in Table 3 were used to calculate the mean percent protection provided by each dose on this parameter. These results are shown in FIG. 8.

Effect of Chronic Treatment with Aerosol HCQ.

Figure 9A:
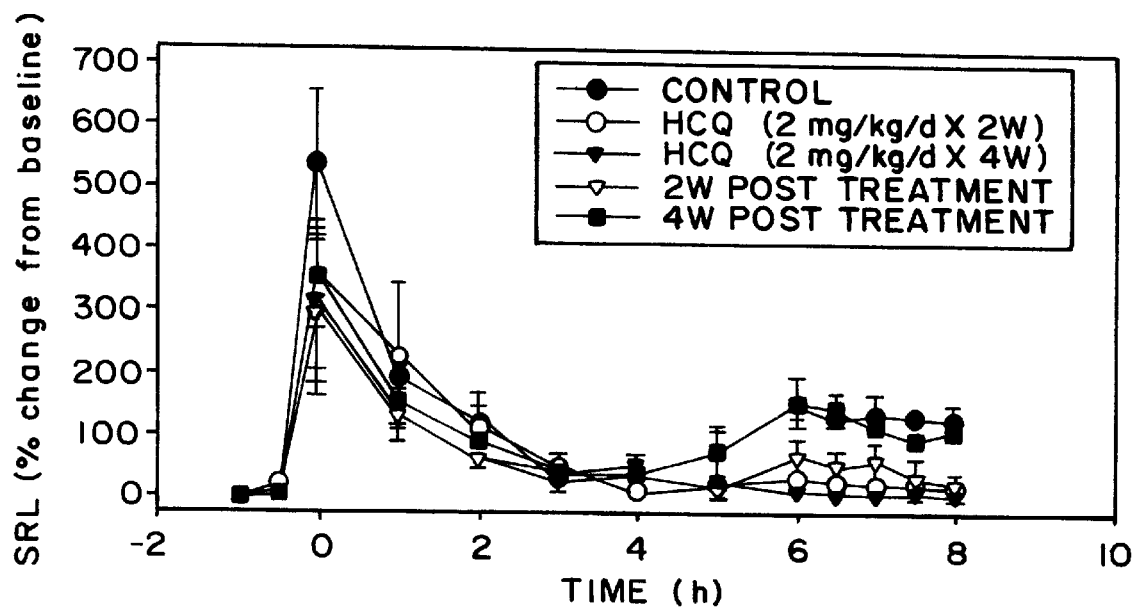
Figure 9B:
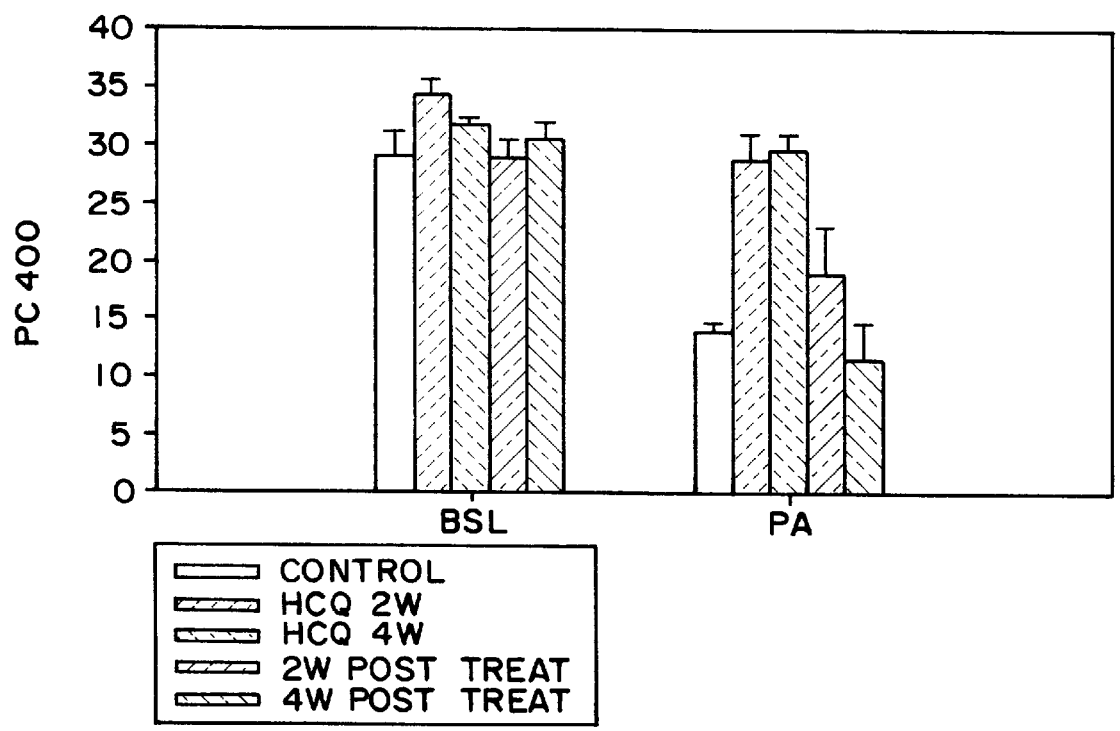
Figure 10:
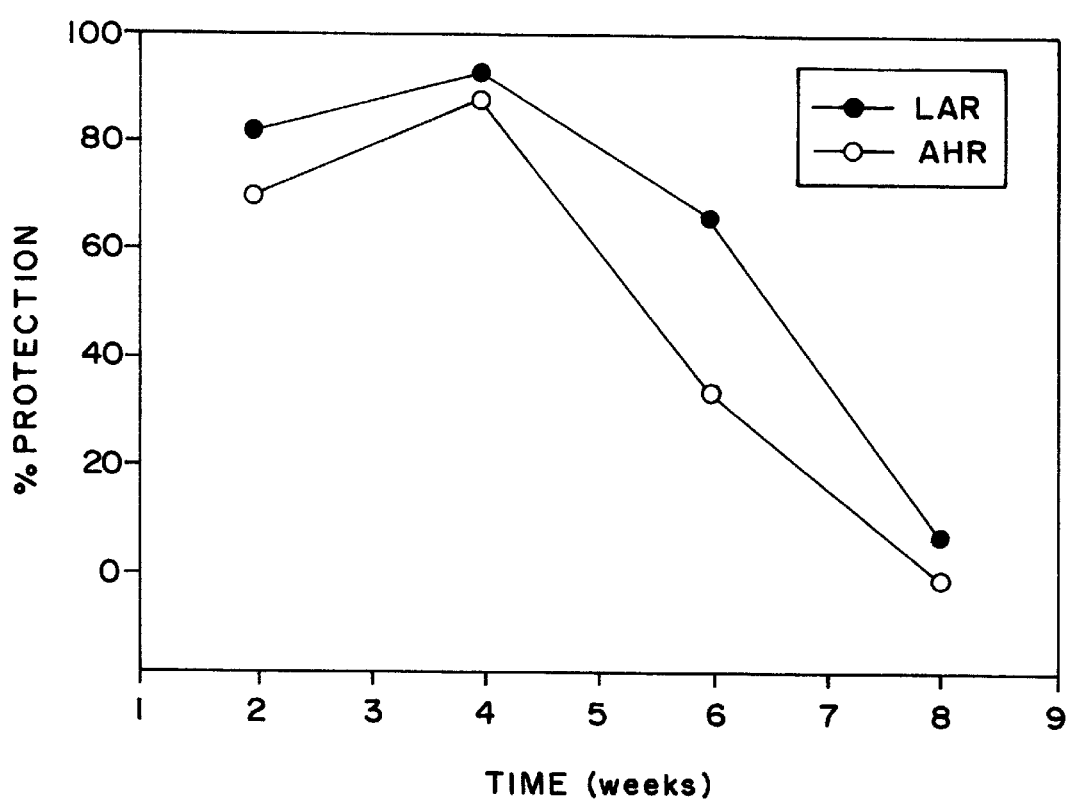

FIG. 9A illustrates the time course of the antigen-induced responses and FIG. 9B the effects on airway responsiveness in the three sheep treated with HCQ aerosol for up to 4 weeks. Overall, there was no effect on the EAR. HCQ aerosol did block the LAR to allergen in these animals (ANOVA, P=0.002). Consistent with the protection against the late response was the protection against the antigen-induced AHR (ANOVA, P=0.018). While it was expected that the 2 and 4 week treatments would be effective in blocking the LAR and AHR, the unexpected result was the carryover effect on these variables seen 2 weeks after treatment had stopped. The effect was more pronounced on the LAR as compared to the AHR. By 4 weeks, the animals' responses had returned to normal. The effect of the different treatment and recovery times on the percent protection of the LAR and AHR are seen in FIG. 10 (calculations were made as described previously). As can be seen, the mean percent protection for both variables increased with treatment time. Likewise, in this protocol, there was still a good protective effect two weeks after stopping drug treatment.

These results show that the dosing strategy in daily dosing may be reduced after a short period of time.

TABLE 3[a]

| TREATMENT | BASELINE | EAR[b] | LAR[b] | AHR[c] |
|---|---|---|---|---|
| Control 1 | 0.93 ± 0.03 | 5.74 ± 1.48 | 2.88 ± 0.24 | 0.43 ± 0.07 |
| HCQ (aerosol) 1 mg/kg/dx2 x4d | 0.93 ± 0.01 | 5.57 ± 1.82 | 1.35 ± 0.15[d,e] | 0.90 ± 0.06[d,g] |
| Control 2 | 0.97 ± 0.03 | 6.27 ± 1.39 | 2.86 ± 0.32 | 0.50 ± 0.48 |
| Control 1 | 1.06 ± 0.04 | 4.64 ± 0.58 | 2.72 ± 0.47 | 0.49 ± 0.07 |
| HCQ (p.o.) 1 mg/kg/dx2 x4d | 0.96 ± 0.01 | 4.64 ± 0.55 | 2.27 ± 0.10 | 0.46 ± 0.06 |
| Control 2 | 0.98 ± 0.03 | 4.08 ± .47 | 2.59 ± 0.34 | 0.48 ± 0.10 |
| Control 1 | 1.01 ± 0.03 | 4.36 ± 0.48 | 2.6 ± 0.12 | 0.45 ± 0.08 |
| HCQ (aerosol) 2 mg/kg/dx4 d | 0.93 ± 0.03 | 3.5 ± 0.73 | 1.34 ± 0.32[d,e] | 1.05 ± 0.14[e] |
| Control 2 | 0.95 ± 0.01 | 4.38 ± 0.38 | 2.35 ± 0.17 | 0.45 ± 0.04 |
| Control | 0.95 ± 0.01 | 4.38 ± 0.38 | 2.35 ± 0.17 | 0.45 ± 0.04 |
| HCQ (aerosol) 2 mg/kg/dx4 d | 0.93 ± 0.02 | 3.53 ± 0.73 | 1.34 ± 0.03[d] | 1.05 ± 0.14[d] |
| HCQ (aerosol) 0.2 mg/kg/d x4d | 0.92 ± 0.02 | 3.95 ± 0.47 | 2.22 ± 0.17[h] | 0.53 ± 0.06[j] |

TABLE 3[a]-continued

| TREATMENT | BASELINE | EAR[b] | LAR[b] | AHR[c] |
|---|---|---|---|---|
| HCQ (aerosol) 0.6 mg/kg/d x4d | 0.93 ± 0.02 | 3.19 ± 0.51 | 1.30 ± 0.18[f] | 0.84 ± 0.15 |
| Control | 0.97 ± 0.03 | 6.27 ± 1.39 | 2.39 ± 0.17 | 0.50 ± 0.05 |
| HCQ (aerosol) 2 mg/kg/dx1 4d | 0.91 ± 0.03 | 4.21 ± 1.68 | 0.78 ± 0.39[f] | 0.85 ± 0.07[f] |
| HCQ (aerosol) 2 mg/kg/dx2 8d | 1.01 ± 0.01 | 4.21 ± 1.16 | 1.22 ± 0.08[d] | 0.94 ± 0.02[d] |
| No Treatment 14d | 1.00 ± 0.06 | 4.17 ± 1.70 | 1.69 ± 0.21 | 0.67 ± 0.16 |
| No Treatment 28d | 0.97 ± 0.02 | 4.35 ± 0.74 | 2.69 ± 0.26[h] | 0.39 ± 0.11[h] |

[a]All results are presented as mean ± SE for n = 3.
[b]Values for baseline, peak EAR (largest value of specific lung resistance for each sheep between 0–4h) and peak LAR (largest value of specific lung resistance for each sheep between 5–8h, irrespective of the time at which it occurred) are specific lung resistance in $cmH_2O.sec^{-1}$.
[c]Values for AHR are post challenge $PC_{400}$: Pre-challenge $PC_{400}$ ratio. A value close to 1 indicates that there is no change in airway responsiveness. Values less than 1 indicate the development of AHR.
[d]$P < 0.05$ vs Control 1;
[e]vs Control 2. $P < 0.05$ vs
[d]Control 1,
[e]Control 2; $P < 0.10$ vs
[f]Control 1,
[g]Control 2; $P < 0.05$ vs
[h]largest dose; $P < 0.10$ vs
[J]largest dose.

Conclusion

The examples above confirm in an allergic sheep model that an anti-malarial agent, when administered locally, such as inhaled hydroxychloroquine, has potent local anti-inflammatory effects and achieves rapid onset of action at lower daily and cumulative dosage than would be expected from systemic administration.

The above preferred embodiments and examples are given to illustrate the scope and spirit of the present invention. These embodiments and examples will make apparent to those skilled in the art other embodiments and examples. These other embodiments and examples are within the contemplation of the present invention.

Therefore, the present invention should be limited only by the appended claims.

What is claimed:

1. A method for treating an inflammatory condition in an animal comprising administering locally to the area of inflammation to said animal an anti-inflammatory effective amount of an anti-malarial compound, wherein said anti-malarial compound is hydroxychloroquine or a pharmaceutically acceptable salt thereof.

2. The method according to claim 1, wherein the inflammatory condition is selected from the group consisting of an inflammatory pulmonary disease, scleritis, epi-scleritis, allergic conjunctivitis, procto-sigmoiditis, allergic rhinitis, arthritis, tendonitis, apthous stomatitis, and inflammatory bowel disease.

3. The method according to claim 2 wherein the inflammatory pulmonary disease is selected from the group consisting of asthma, chronic obstructive pulmonary disease, allergic bronchopulmonary aspergillosis, and sarcoidosis.

4. The method according to claim 1, wherein the anti-malarial compound is locally administered to the lungs.

5. The method according to claim 4, wherein the anti-malarial compound is locally administered via inhalation.

6. The method according to claim 5, wherein the anti-malarial compound is formulated for aerosol delivery or formulated as dry powder.

7. The method according to claim 1 wherein the inflammatory condition is asthma.

8. The method according to claim 1, wherein the anti-malarial compound is formulated as an eye drop, a suppository, a nasal spray, or an oral paste.

9. A method for treating asthma, comprising administering an anti-inflammatory effective amount of hydroxychloroquine via inhalation to a patient with asthma.

* * * * *